(12) United States Patent
El-Shall et al.

(10) Patent No.: US 8,871,171 B2
(45) Date of Patent: Oct. 28, 2014

(54) PRODUCTION OF GRAPHENE AND NANOPARTICLE CATALYSTS SUPPORTED ON GRAPHENE USING MICROWAVE RADIATION

(75) Inventors: M. Samy El-Shall, Richmond, VA (US); Victor Abdelsayed, Morgantown, WV (US); Hassan M. A. Hassan, Richmond, VA (US); Abd El Rahman S. Khder, Richmond, VA (US); Khaled M. Abouzeid, Richmond, VA (US); Qilin Dai, Richmond, VA (US); Parichehr Afshani, Richmond, VA (US); Frank Gupton, Richmond, VA (US); Ali R. Siamaki, Richmond, VA (US); Zeid Abdullah M. Alothman, Riyadh (SA); Hamad Zaid Alkhathlan, Riyadh (SA)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 13/636,712

(22) PCT Filed: Mar. 25, 2011

(86) PCT No.: PCT/US2011/029998
§ 371 (c)(1),
(2), (4) Date: Apr. 22, 2013

(87) PCT Pub. No.: WO2011/119961
PCT Pub. Date: Sep. 29, 2011

(65) Prior Publication Data
US 2013/0211106 A1 Aug. 15, 2013

Related U.S. Application Data

(60) Provisional application No. 61/317,860, filed on Mar. 26, 2010, provisional application No. 61/322,376, filed on Apr. 9, 2010, provisional application No. 61/362,866, filed on Jul. 9, 2010.

(51) Int. Cl.
*C01B 31/02* (2006.01)
*B01J 37/34* (2006.01)
(Continued)

(52) U.S. Cl.
CPC ........... *B01J 23/44* (2013.01); *B01J 37/346* (2013.01); *B01J 35/002* (2013.01);
(Continued)

(58) Field of Classification Search
USPC ............. 423/445 B; 502/262, 325, 344, 349, 502/340, 355
See application file for complete search history.

(56) References Cited

U.S. PATENT DOCUMENTS

2005/0271574 A1 12/2005 Jang et al.
2008/0206124 A1 8/2008 Jang et al.
(Continued)

FOREIGN PATENT DOCUMENTS

WO  WO 2007093081 A1 * 8/2007

OTHER PUBLICATIONS

Hasan, H. et al. "Microwave synthesis of graphene sheets supporting metal nanocrystals in aqueous and organic media" J. Mater. Chem., 2009, 19, 3832-3837.*

(Continued)

*Primary Examiner* — Richard M Rump
(74) *Attorney, Agent, or Firm* — Whitham, Curtis, Christofferson & Cook, P.C.

(57) ABSTRACT

Microwave irradiation is used to synthesize graphene and metallic nanocatalysts supported on graphene either by solid or solution phase. In solid phase methods, no solvents or additional reducing agents are required so the methods are "environmentally friendly" and economical, and the graphene and nanocatalysts are substantially free of residual contaminants. Recyclable, high efficiency Pd nanocatylysts are prepared by these methods.

9 Claims, 21 Drawing Sheets

(51) Int. Cl.
- *B01J 35/00* (2006.01)
- *B01J 19/12* (2006.01)
- *C07B 37/04* (2006.01)
- *B01J 21/18* (2006.01)
- *B01J 23/75* (2006.01)
- *B82Y 30/00* (2011.01)
- *B01J 23/50* (2006.01)
- *B01J 23/755* (2006.01)
- *B01J 23/44* (2006.01)
- *B01J 23/745* (2006.01)
- *B01J 23/72* (2006.01)
- *B82Y 40/00* (2011.01)
- *C01B 31/04* (2006.01)

(52) U.S. Cl.
CPC ............... *B01J 19/126* (2013.01); *C07B 37/04* (2013.01); *B01J 21/18* (2013.01); *B01J 23/75* (2013.01); *B82Y 30/00* (2013.01); *B01J 23/50* (2013.01); *B01J 23/755* (2013.01); *B01J 23/745* (2013.01); *B01J 23/72* (2013.01); *B82Y 40/00* (2013.01); *B01J 35/006* (2013.01); *C01B 31/0476* (2013.01); *B01J 35/0013* (2013.01)
USPC ...................................... 423/445 B; 502/262

(56) References Cited

U.S. PATENT DOCUMENTS

2009/0110627 A1  4/2009  Choi et al.
2009/0155161 A1  6/2009  Yoon et al.

OTHER PUBLICATIONS

Palladium Nanoparticles on Graphite Oxide and Its Functionalized Graphene Derivatives as Highly Active Catalysts for the Suzuki—Miyaura Coupling Reaction Gil M. Scheuermann, Luigi Rumi, Peter Steurer, Willi Bannwarth, and Rolf Mülhaupt Journal of the American Chemical Society 2009 131 (23), 8262-8270.*

Carbon Nanotubes Decorated with Palladium Nanoparticles: Synthesis, Characterization, and Catalytic Activity Nikolaos Karousis, Georgia-Eleni Tsotsou, Fabrizio Evangelista, Petra Rudolf, Nikitas Ragoussis, and Nikos Tagmatarchis The Journal of Physical Chemistry C 2008 112 (35), 13463-13469.*

Avelino Corma, Hermenegildo Garcia, Antonio Leyva, Catalytic activity of palladium supported on single wall carbon nanotubes compared to palladium supported on activated carbon: Study of the Heck and Suzuki couplings, aerobic alcohol oxidation and selective hydrogenation, Journal of Molecular Catalysis A: Chemical, vol. 230, Issues 1-2, Apr. 2005.*

Sokolov, V. I., et al. "New synthesis of palladium catalyst immobilized on carbon nanotubes and its activity in certain organic reactions." Nanotechnologies in Russia 3.9-10 (2008): 570-574.*

Seger, Brian, and Prashant V. Kamat. "Electrocatalytically active graphene-platinum nanocomposites. Role of 2-D carbon support in PEM fuel cells." The Journal of Physical Chemistry C 113.19 (2009): 7990-7995.*

Zhu, Yanwu, et al. "Microwave assisted exfoliation and reduction of graphite oxide for ultracapacitors." Carbon 48.7 (2010): 2118-2122.*

Phan, N. T., et al. "On the Nature of the Active Species in Palladium Catalyzed Mizoroki—Heck and Suzuki—Miyaura Couplings—Homogeneous or Heterogeneous Catalysis, A Critical Review" Advanced Synthesis & Catalysis vol. 348, Issue 6, pp. 609-679, Apr. 2006.*

* cited by examiner

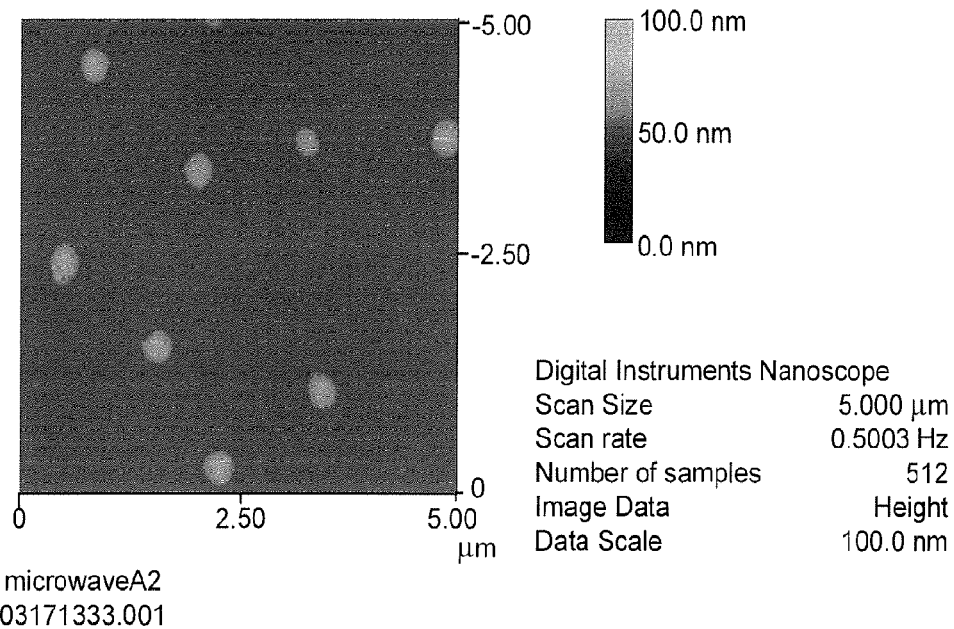
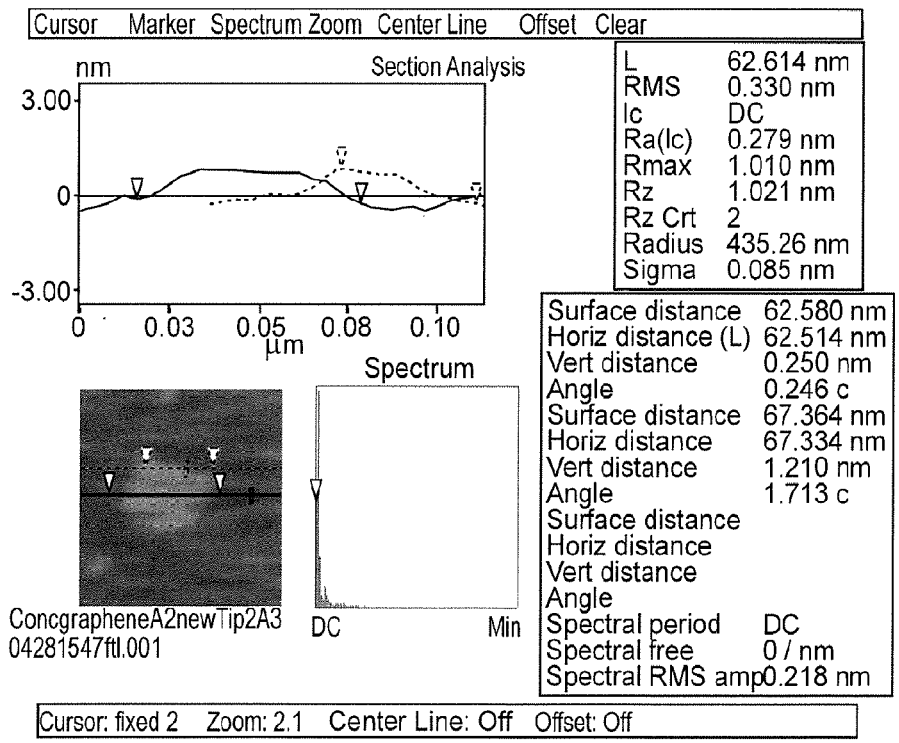
*Figure 2*

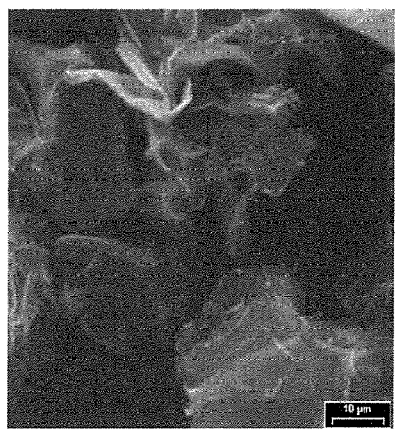
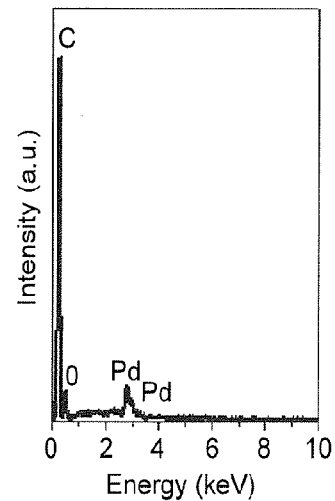
Figure 9A
Figure 9B
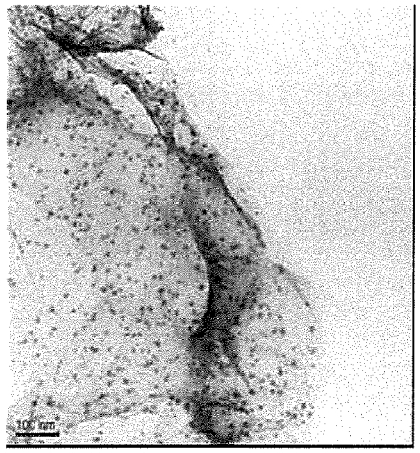
Figure 10A
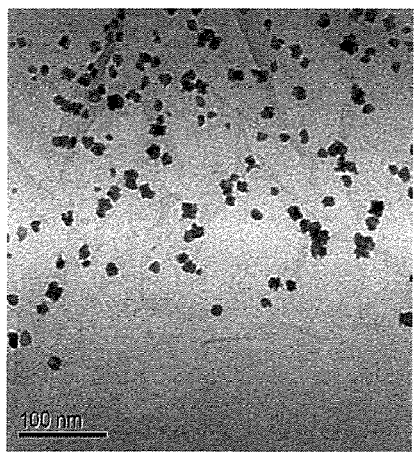
Figure 10B

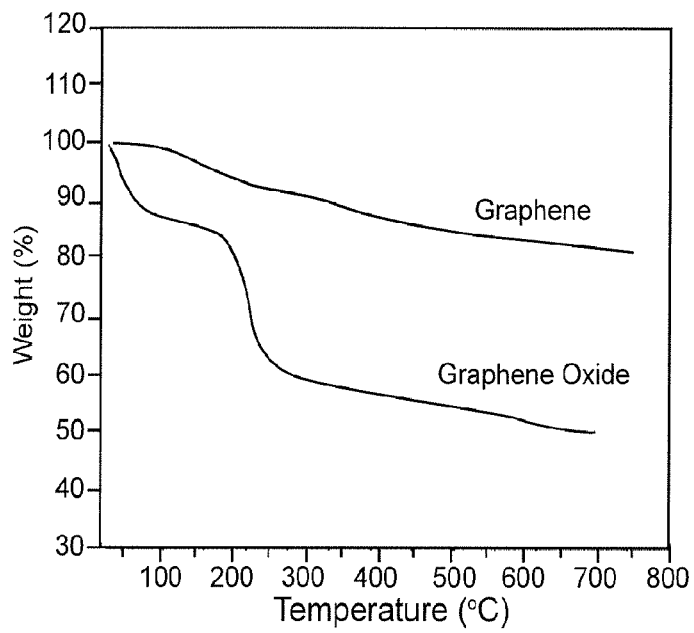
*Figure 21*
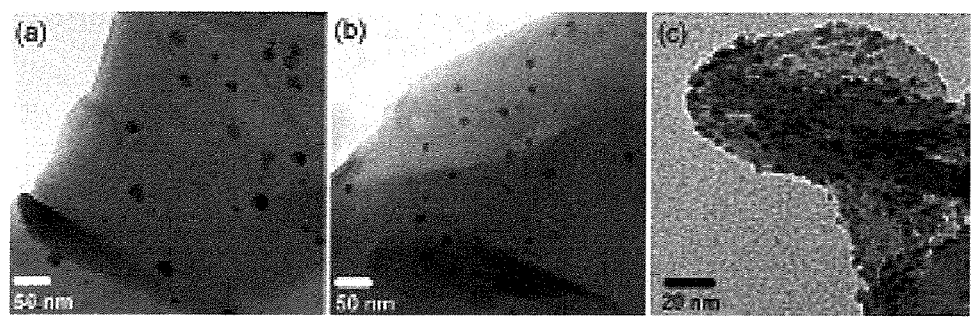
*Figure 22A*  *Figure 22B*  *Figure 22C*

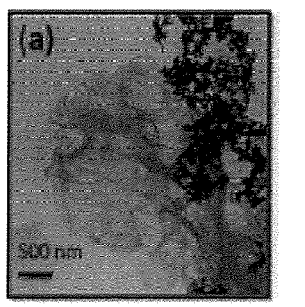
Figure 23A
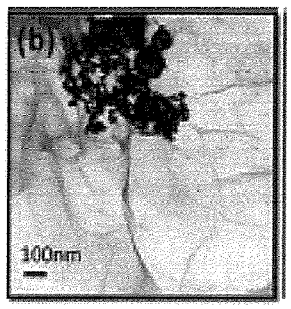
Figure 23B
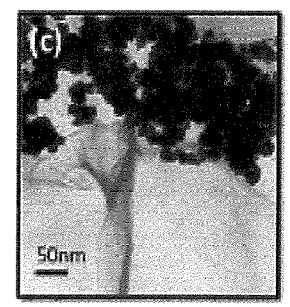
Figure 23C
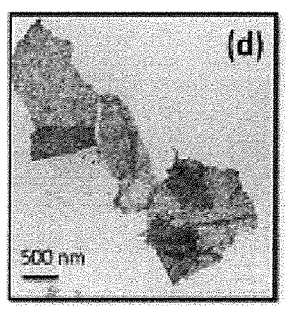
Figure 23D
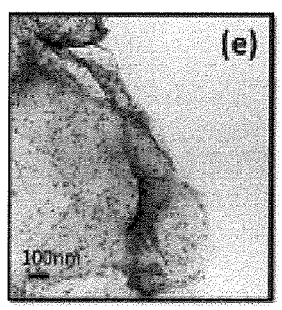
Figure 23E
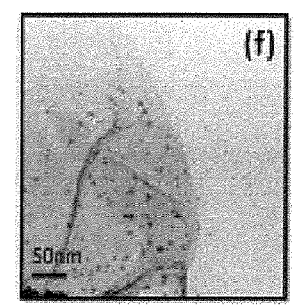
Figure 23F
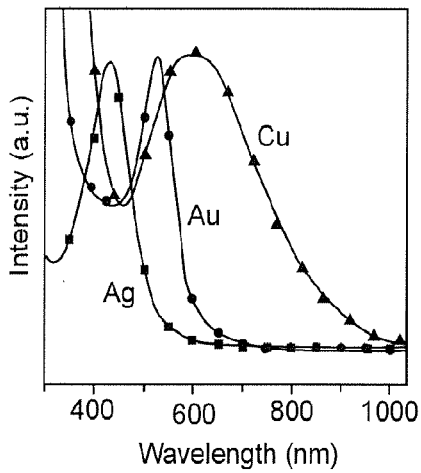
Figure 24A
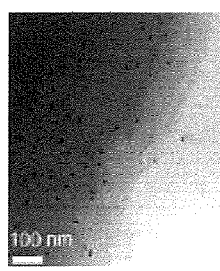
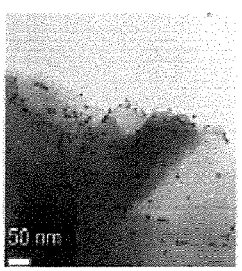
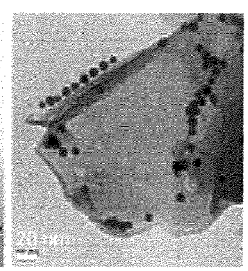
Figure 24B

US 8,871,171 B2

PRODUCTION OF GRAPHENE AND NANOPARTICLE CATALYSTS SUPPORTED ON GRAPHENE USING MICROWAVE RADIATION

BACKGROUND OF THE INVENTION

1. Field of the Invention

The invention generally relates to methods of producing graphene and nanoparticle catalysts supported on graphene using microwave radiation. In particular, the invention provides methods and apparatuses which employ microwave radiation to reduce 1) solid graphite oxide (GO) to graphene without the use of additional reducing agents, or 2) solution phase GO; as well as solid and solution phase methods to reduce a mixture of GO plus one or more metals to produce nanoparticle catalysts supported on graphene.

2. Background of the Invention

The recent extensive interest in graphene associated with its unique hexagonal atomic layer structure and unusual properties, including the highest intrinsic carrier mobility at room temperature of all known materials, is motivated by the development of new composite materials for nanoelectronics, supercapacitors, batteries, photovoltaics, and related devices. Other properties of graphene such as the high thermal, chemical, and mechanical stability as well as high surface area also represent desirable characteristics as a 2-D catalyst support for metallic and bimetallic nanoparticles for a variety of applications in heterogeneous catalysis, sensors, hydrogen storage, and energy conversion.

Recent advances in the production of graphene sheets through the reduction of exfoliated graphite oxide (GO) have provided efficient approaches for the large scale production of chemically converted graphene (CCG) sheets. However, chemical reduction methods suffer from the difficulty of controlling the reduction process and residual contamination by the chemical reducing agents. This can cause detrimental effects, particularly for electronic applications of graphene. Therefore, there is a need for developing deoxygenation/reduction methods that do not rely on the use of chemicals or high temperatures. Recently, a flash reduction process was reported for the deoxygenation of GO films by photothermal heating of camera flash lights.[1,2] However, the method does not provide a solution process for the synthesis of individual graphene sheets because it was only applied to thin dry films of GO. Similarly, femtosecond laser pulses have been used for imprinting and patterning of 55 nm thick GO films, which resulted in partial reduction of the GO multilayer film with reduced depth of 35-25 nm, but the laser reduction process of individual GO sheets dispersed in water was not demonstrated.[3]

There is an ongoing need to provide improved, diversified and efficient methods for producing graphene and graphene supported nanoparticle catalysts.

SUMMARY OF THE INVENTION

The invention provides methods of producing graphene using microwave irradiation of solution phase graphite oxide (GO) using a chemical reducing agent, or of solid GO under the effect of microwave plasma without the use of a chemical reducing agent. Since chemical reducing agents and solvents are not required in the latter methods, they are environmentally advantageous (fewer noxious waste products) and cost effective. The method also encompasses the simultaneous reduction, using microwave energy, of solution or solid phase graphite oxide together with a variety of metals, resulting in the dispersion of metallic nanoparticles supported on the large surface area of the thermally stable 2D graphene sheets. The graphene supported metal nanoparticles are advantageously used as catalysts, and, when produced from solid reactants without chemical reducing agents and solvents, such nanocatalysts are not contaminated with residual solvent or reducing agent.

In other embodiments, the invention provides super-active, super-efficient recyclable palladium nanocatalysts comprising Pd supported on graphene sheets (Pd/G catalysts), and uses for the same to carry out reactions. These Pd nanocatalysts are prepared using microwave irradiation by either 1) using solid reactants as described above, under the effect of microwave plasma without the use of a chemical reducing agent; or 2) in solution with the use of a chemical reducing agent.

It is an object of this invention to provide a method of producing graphene. The method comprises the step of irradiating solid graphite oxide (GO) with microwave radiation. In one embodiment, the method is carried out in the absence of chemical reducing agents. In another embodiment, the GO provided in said providing step is mixed with at least one metal or metal alloy and the exposing step produces metal or metal alloy nanoparticles supported on the graphene. In yet another embodiment, the at least one metal or metal alloy is selected from the group consisting of Au, Ag, Pd. Co, Pd, Co, Au, Ag, Cu, Pt, Ni, Fe, Mn, Cr, V, Ti, Sc, Ce, Pr, Nd, Sm, Gd, Hom Er, Yb, Al, Ga, Sn, Pb, In, Mg, Ca, Sr, Na, K, Rb, and Cs. In some embodiments, the at least one metal or metal alloy is Pd.

The invention further provides a method of catalyzing chemical coupling of at least two reactants of interest at very high yields (above 60%, 70%, 80% and 90%). The method comprises the steps of 1) providing a Pd catalyst comprising nanoparticulate Pd supported on graphene, wherein said Pd catalyst is produced by irradiating a mixture of graphite oxide (GO) and Pd metal with microwave radiation; and 2) combining the at least two reactants of interest in the presence of the Pd catalyst and under conditions which allow the Pd catalyst to catalyze the chemical coupling of the at least two reactants of interest. In some embodiments, the Pd catalyst is active for at least 5 coupling cycles.

In one embodiment, the chemical coupling is a Suzuki cross-coupling reaction; and in this embodiment, a turnover frequency of the Pd catalyst may be at least 100,000 h$^{-1}$, and the product yield of the Suzuki cross-coupling reaction is at least 65%.

In other embodiments, the chemical coupling is a Heck cross-coupling reaction. In these embodiments, the product yield of the Heck cross-coupling reaction is at least 84%.

In yet other embodiments, the chemical coupling is a Sonogashira cross-coupling coupling reaction. In these embodiments, the product yield of the Sonogashira cross-coupling reaction is at least 88%.

In one embodiment of the method, the Pd catalyst is prepared by irradiating solid GO mixed with a Pd salt (e.g. Pd nitrate, Pd acetate, etc.) with microwave radiation under the effect of microwave plasma, and the Pd catalyst that is formed is substantially free of residual contaminants.

The invention also provides a method of producing graphene, comprising the step of irradiating a solution of graphite oxide (GO) with microwave radiation. In some embodiments, the solution of GO further comprises at least one metal or metal alloy (usually a salt thereof) and the exposing step produces metal or metal alloy nanoparticles supported on the graphene. Exemplary metals include Au, Ag, CoPd, Co, Au, Ag, Cu, Pt, Ni, Fe, Mn, Cr, V, Ti, Sc, Ce, Pr, Nd, Sm, Gd, Hom Er, Yb, Al, Ga, Sn, Pb, In, Mg, Ca, Sr, Na, K, Rb, and Cs. In one embodiment, the at least one metal or metal alloy is Pd.

BRIEF DESCRIPTION OF THE DRAWINGS

FIG. 2. Atomic force microscopy (AFM) data of graphene sheets produced by MWI of solid graphite oxide.

FIGS. 9A and B. (a) SEM image and (b) EDS analysis of Pd/G prepared by the HH-MWI method.

FIGS. 10A and B. TEM images of (a) 7.9 wt. % Pd/G and (b) 6.4 wt. % Pd/GO prepared by MWI of a mixture of graphite oxide (GO) and palladium nitrate in the presence and absence of hydrazine hydrate, respectively.

FIG. 21. Comparison of the TGA plots of the graphite oxide and the chemically converted graphene sheets using MWI of GO in the presence of HH.

FIG. 22A-C. TEM images of the chemically converted graphene sheets containing (a) Pd, (b) Cu and (c) CuPd nanoparticles prepared by the simultaneous reduction of GO and the appropriate metal salt in water using hydrazine hydrate under MWI.

FIG. 23A-F. TEM images of the chemically converted graphene sheets containing Pd nanoparticles prepared by mixing separately prepared Pd nanoparticles and CCG sheets (a, b, c), and simultaneous reduction of GO and Pd nitrate in water using hydrazine hydrate under MWI (d, e, f).

FIGS. 24A and B. (a) UV-Vis absorptions of the toluene suspensions of the graphene sheets containing Ag, Au and Cu nanoparticles prepared by the simultaneous reduction of GO and the appropriate metal salt using oleylamine as a reducing agent under MWI. (b) TEM images of the graphene sheets containing Au nanoparticles.

DETAILED DESCRIPTION

Figure 1A:
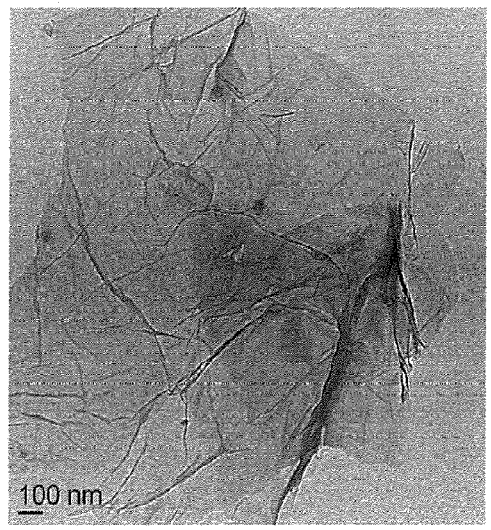
FIG. 1A-H. Transmission electron microscopy (TEM) images of graphene sheets produced by microwave irradiation (MWI) of solid graphite oxide.
Figure 1B:
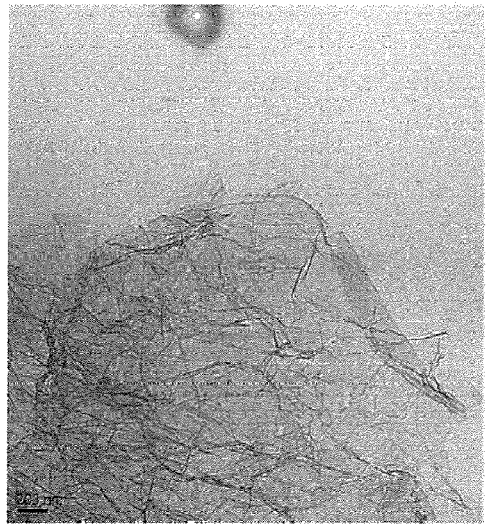
Figure 1C:
Figure 1D:
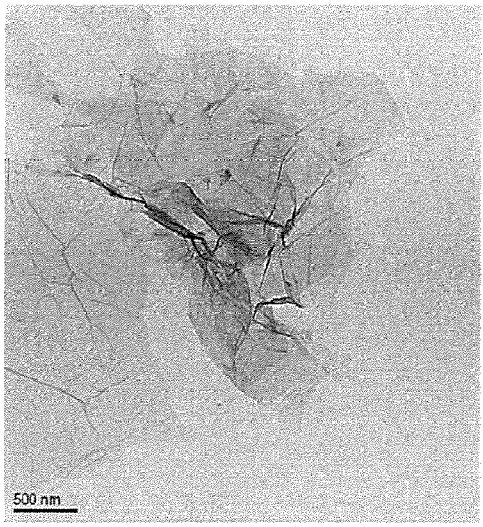
Figure 1E:
Figure 1F:
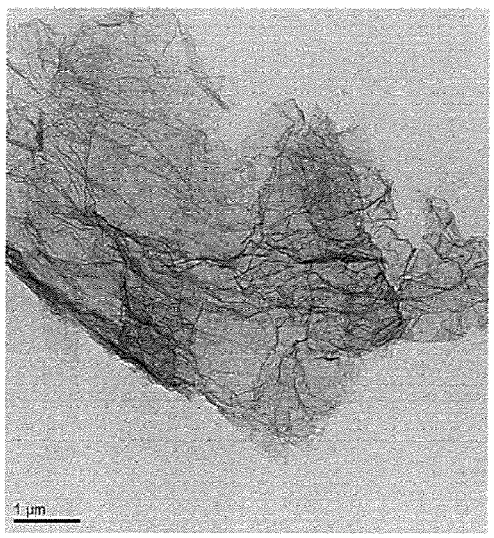
Figure 1G:
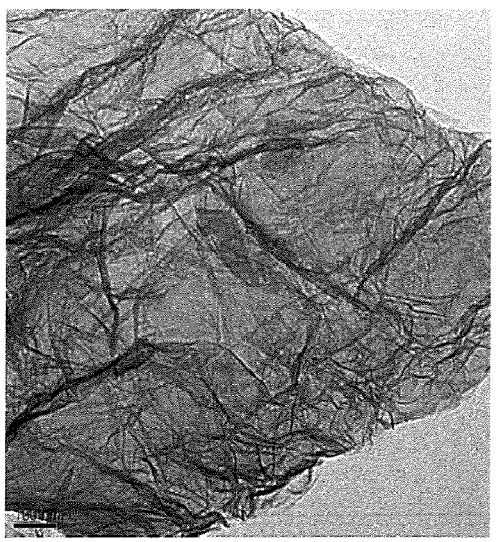
Figure 1H:
Figure 3A:
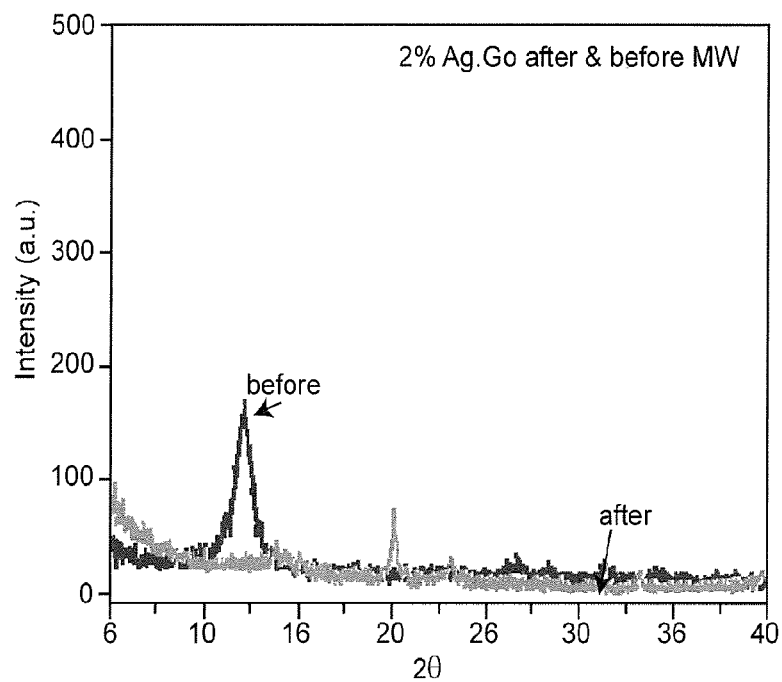
FIG. 3A-F. X-ray diffraction (XRD) patterns of GO containing 2% metal precursors before and after the MWI of the solid. A, silver; B, cobalt; C, copper; D, iron; E, nickel; F, palladium.
Figure 3B:
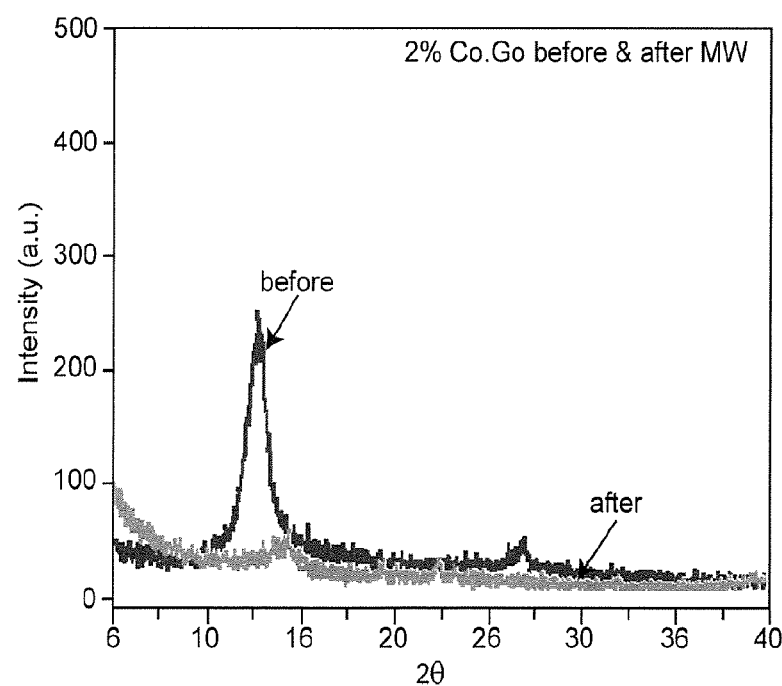
Figure 3C:
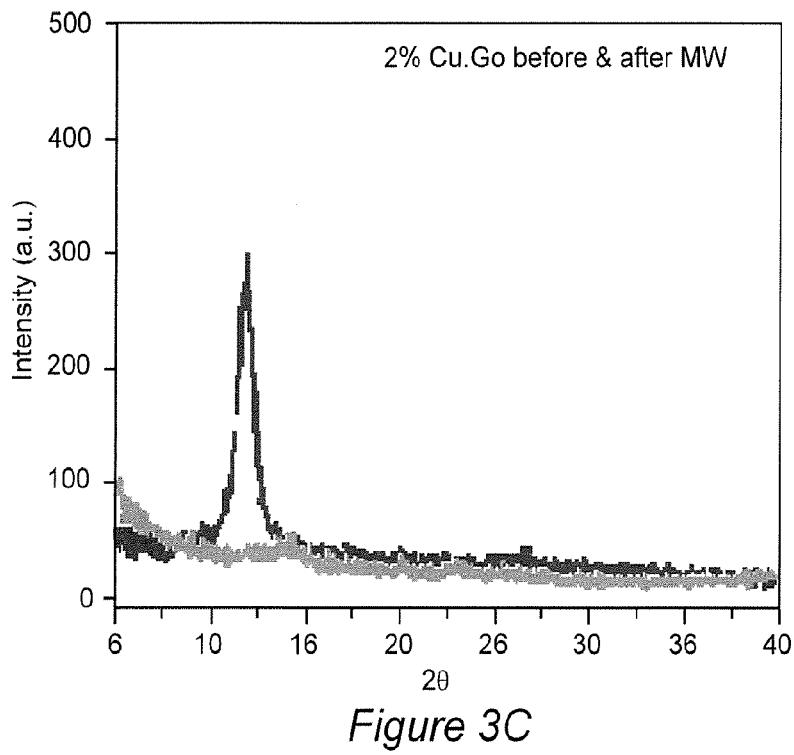
Figure 3D:
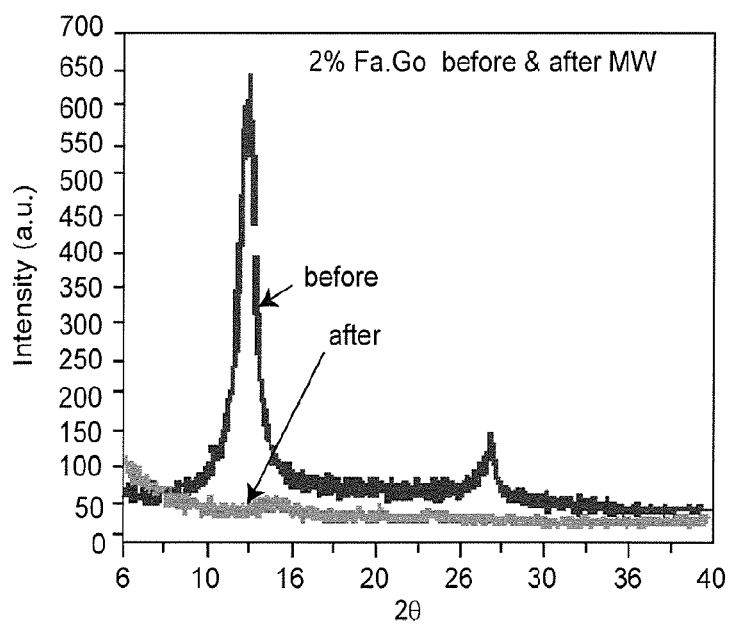
Figure 3E:
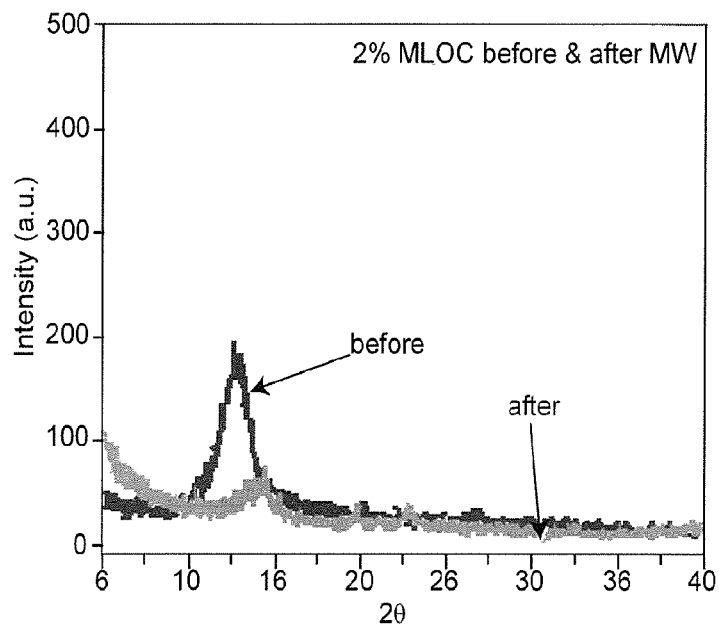
Figure 3F:
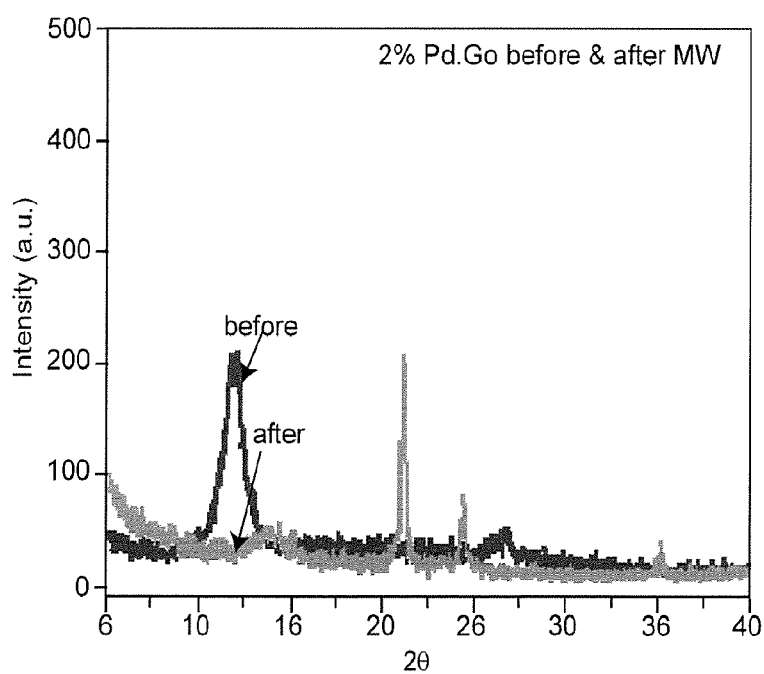
Figure 4A:
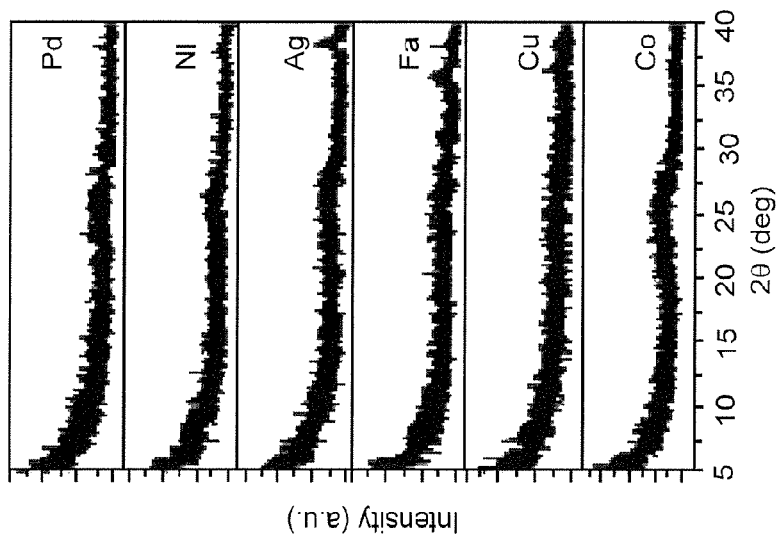
FIG. 4. XRD patterns of GO containing 5% metal precursors A, before and B, after the MWI of the solid.
Figure 4B:
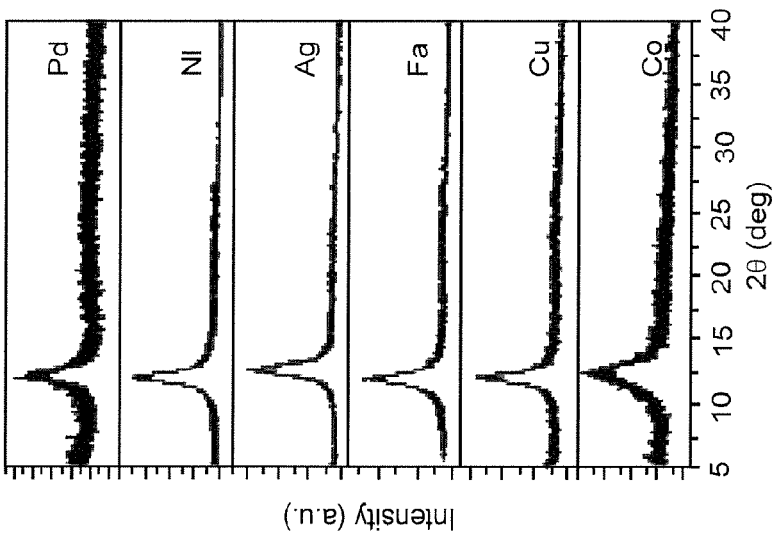

The invention encompasses the synthesis of graphene and metallic nanocatylsts supported on graphene using microwave energy. In some embodiments, the synthesis methods are carried out with reactants in solution (e.g. aqueous and/or aqueous plus suitable organic solvents). In other embodiments, the invention encompasses the synthesis of graphene from solid graphite oxide (GO) by a fast and simple process that does not involve the use of chemical reducing agents and yet allows the production of high quality graphene. According to this embodiment of the invention, graphene sheets are produced on substrates by exposing solid graphite oxide to microwave irradiation under the plasma energy produced by microwave-solid interaction without the use of additional reducing agents. In some embodiments, one or more solid metals of interest are mixed with the solid GO, and exposure of these solid reactants to microwave irradiation produces nanoparticle catalysts supported on a sheet of high quality graphene. This simultaneous reduction of solid GO and one or more of a variety of metal salts results in the dispersion of metallic and bimetallic nanoparticle catalysts supported on the large surface area of a thermally stable 2D graphene sheets.

A significant advantage of using the microwave reduction of solid GO methods described herein to prepare graphene and metal nanoparticles supported on graphene is to avoid the use of toxic chemical reducing agents and thus provide a "green", environmentally responsible approach for the synthesis and processing of graphene and metal-graphene nanocomposites. Also, especially for applications in catalysis, the absence of traces of reducing or capping agents from the surface of the supported nanocatalysts is advantageous. In addition, the present methods provide better control of the reduction processes without the need of high temperatures. The method also encompasses the facile simultaneous reduction of two or more different metal ions on the graphene surface which produces graphene nanocomposites with desirable catalytic, magnetic and optical properties.

In a further embodiment, the invention also provides super-efficient and recyclable metallic nanocatalysts supported on graphene sheets, in particular, Pd nanocatalyst. Such Pd catalysts may be made using solid reactants as described herein, or, alternatively, by using a methodology that employs additional reducing agents as described below. The nanocatalysts are super-active and super-efficient. For example, prior art Pd catalysts typically require about 8 hours to catalyze a Suzuki reaction. However, the Pd nanocatalysts of the invention require only about 20 minutes to carry out the same reaction at room temperature, and only about 5 minutes at 80° C. (For the purposes of this application, "super-active" and "super-efficient" catalysts are those that are 10× or 100× or more active than comparable catalysts. Because they are so active, the catalysts of the invention are ideal for use in, for example, high throughput manufacturing processes and/or, for example, for use in continuous flow chemical syntheses. The reason for this high efficiency is likely the uniform distribution of the nanoparticulate metal clusters that are dispersed (supported) on the graphene support. Without being bound by theory, it is believed that as the metallic-graphene catalyst is formed using the novel methods of the invention, during conversion of GO to graphene, the graphene forms around the nanoparticulate metal and prevents or limits the extent of metal-metal interaction or reaction. In other words, concomitant with GO reduction, graphene forms around the metal (e.g. Pd) nanoparticles. Thus, the sizes of the metallic nanoparticles may be limited (large agglomerations are not formed and the nanoparticles tend to be of a similar size, i.e. the sizes of individual nanoparticles are more uniform, and the distribution of the metallic nanoparticles on or across the support is substantially uniform or equal, particularly when considered as numbers of metal clusters per $nm^2$, e.g. the density of nanoparticles per unit surface area (e.g. $nm^2$). Those of skill in the art will recognize that "substantially uniform" means that such distributions may vary somewhat and are generally as represented in FIG. 10B and throughout this application. As can be seen from the electron micrographs presented e.g. in FIG. 10B, the numbers generally range from e.g. about 1 to about 25 (or more e.g. 1-about 30, 40 or 50) metal particles per 100 $nm^2$ in average density, and may be in the range of from about 2-20 per 100 $nm^2$, or about 5-15 per 100 $nm^2$; or the ranges may be even narrower, over the majority of the surface area of the graphene (e.g. over at least about 50% of the surface area or catalytic area of the graphene, e.g. the area where metal nanoparticles are located). If higher (or lower) density catalysts are made, the densities of distribution may also be higher (or lower) but the relative average ranges of density remain approximately the same.

The following definitions are provided:

By "graphene" we mean $sp^2$-bonded carbon atoms that are densely packed in a one-atom-thick planar sheet. Graphene atoms form a honeycomb or "chicken-wire" atomic scale crystal lattice made of carbon atoms and their bonds. The crystalline or "flake" form of graphite consists of many graphene sheets stacked together.

"Graphite oxide" (formerly called graphitic oxide or graphitic acid) as used herein, refers to a compound of carbon, oxygen, and hydrogen in variable ratios, obtained by treating graphite with strong oxidizers. The maximally oxidized bulk product is a yellow solid with C:O ratio between 2.1 and 2.9, that retains the layer structure of graphite but with a much larger and irregular spacing. The structure and properties of graphite oxide are variable and depend on the particular synthesis method and degree of oxidation. It typically preserves the layer structure of the parent graphite, but the layers are buckled and the interlayer spacing is about two times larger (~7 Å) than that of graphite. Strictly speaking "oxide" is an incorrect but historically established name. Besides oxygen, epoxide groups (bridging oxygen atoms), and other functional groups experimentally found are in graphite oxide, e.g. carbonyl (=CO), hydroxyl (—OH), phenol groups, especially attached to the edges of each layer. There is evidence of "buckling" (deviation from planarity) of the layers and the detailed structure is still not understood due to the strong disorder and irregular packing of the layers. Graphene oxide layers are about 1.1±0.2 nm thick.

By "oxidation" we mean the loss of electrons.

By "reduction" we mean the gain of electrons.

By "nanoparticle" we mean particles which, in terms of diameter, range between from about 1 to about 10,000 nanometers (nms), or from about 10 to about 5000 nm, or even from about 50 to about 2500 nm, or from about 100 to about 1000 nm. In some embodiments, a "nano-sized" particle has a diameter in the range of from about 1 to about 20 nm, e.g. about 1, 2, 3, 4, 5, 6, 7, 8, 9, 10, 11, 12, 13, 14, 15, 16, 17, 18, 19, or 20 nm, or even about 25, 30, 35, 40 or 45 nm. Such nanoparticles behave as a whole unit in terms their properties. This definition applies equally to such terms as "nano-sized", "nanoparticulate", "nanocatalyst", "nanocluster", etc., as used herein.

"Microwave radiation" refers to electromagnetic waves with wavelengths ranging from as long as one meter to as short as one millimeter, or equivalently, with frequencies between 300 MHz (0.3 GHz) and 300 GHz. This broad definition includes both ultra high frequency (UHF) and extremely high frequency (EHF; millimeter waves). Those of skill in the art may differ with respect to the precise boundaries. However, in all cases, "microwave" includes the entire Super high frequency (or SHF) refers to radio frequencies (RF) in the range of (3 to 30 GHz, 10 to 1 cm) at a minimum, with radio frequency (RF) engineering often putting the lower boundary at 1 GHz (30 cm), and the upper around 100 GHz (3 mm).

By "catalyst" we mean a substance that alters the velocity of a chemical reaction and may be recovered essentially unaltered in form and amount at the end of the reaction, i.e. a catalyst is not consumed by the reaction itself. Catalytic reactions generally have a lower rate-limiting free energy of activation than the corresponding uncatalyzed reaction, resulting in higher reaction rate at the same temperature.

By "coupling reaction" we mean the range of reactions in organometallic chemistry where two hydrocarbon fragments are coupled with the aid of a metal catalyst supported by suitable ligands. Coupling reactions include both cross couplings (reaction between two chemically distinct partners) and homocouplings (couples a molecule to itself, often in a reductive or oxidative fashion).

By "solution" or "liquid" phase, we mean that the reactants are present in a liquid e.g. dissolved or otherwise suspended or dispersed in the liquid. The reactants may be fully dissolved in solution or made be in the form of (usually) fine particles which are suspended or dispersed in the liquid.

Graphene Synthesis Via Microwave Irradiation of Reactants in Solution Using a Reducing Agent In one embodiment a mixture of graphite oxide soluble in water or in a mixture of organic solvents and surfactants is converted into graphene by a microwave assisted chemical reduction process. The same method is used in the presence of a metal salt soluble in water in the synthesis of metal nanoparticles supported on graphene. This method provides a facile and scalable chemical reduction method assisted by microwave irradiation for the synthesis of chemically converted graphene sheets and metal nanoparticles dispersed on the graphene sheets. The method allows rapid chemical reduction of exfoliated graphite oxide (GO) using a variety of reducing agents in either aqueous or organic media. It also allows the simultaneous reduction of GO and a variety of metal salts thus resulting in the dispersion of metallic and bimetallic nanoparticles supported on the large surface area of the thermally stable 2D graphene sheets Liquid media that can be used to disperse GO in a manner suitable for microwave irradiation include but are not limited to: aqueous-based media such as water; aqueous solutions of water and alcohols such as ethanol (e.g. from about 10 to about 90% ETOH, or from about 20 to about 80%, or from about 30 to about 70%, or from about 40 to about 60%, and usually about 50% ETOH); solutions of polyethylene glycol (PEG) in water (e.g. from about 1% to about 10%, e.g. about 1, 2, 3, 4, 5, 6, 7, 8, 9 or 10% PEG in water); other alcohols such as methanol, isopropanol, etc., or other polar liquids such as acetonitrile, dimethylsulfoxide (DMSO), etc. Examples of other suitable solvents include but are not limited to a broad range of polar and non-polar organic and aqueous solvents and solvent systems, including but not limited to hydrocarbons, ethers, alcohols, nitriles, etc., as well as those listed in U.S. Pat. Nos. 7,892,413; 7,894,694; 7,896,809; 7,888,631 and 7,897,195, the complete contents of each of which is hereby incorporated by reference. Further, in some embodiments, surfactants may be added, examples of which include but are not limited to those listed in, for example, U.S. Pat. No. 7,105,229 (Anderson) the complete contents of which is hereby incorporated by reference. Solvents listed in Anderson may also be used.

The concentration of GO in the medium that is irradiated is generally in the range of from about 0.1 mg/mL (or even less) to about 10 mg/mL (or greater), and is usually in the range of from about 1 mg/mL to about 5 mg/mL.

The length of exposure of GO to microwave energy will vary depending on the type and strength of radiation that is used, the concentration of GO in the suspension, and the solution volume. Generally, these variables are adjusted so that the time of radiation is in the range of from about 1 to about 10 minutes, i.e. about 1, 2, 3, 4, 5, 6, 7, 8, 9, or 10 minutes. Further, several cycles of irradiation may be used, e.g. from about 1 to about 10 or more cycles (i.e. about 1, 2, 3, 4, 5, 6, 7, 8, 9, or 10 cycles) with each cycle including an exposure of the GO to the source of radiation of at least about one minute or more, as described above.

Prior to exposing the GO to microwave energy, the GO may be exfoliated in order to separate the layers. This is generally accomplished by dispersing GO in water using ultrasonic or stirring until a clear well-dispersed solution is obtained with a golden yellow color.

The starting temperature at which the conversion of GO to graphene is carried out is generally ambient (i.e. room) temperature, i.e. about 20 to 25° C. (68 to 77° F.), although this need not always be the case. In some embodiments, the temperature may be higher (e.g. up to about 37° C.) or lower (e.g. as low as about 1-2° C.) while still successfully producing graphene. It is also possible to start with frozen GO solution (below 0° C., e.g. −50° C. or −10° C., etc.). Those of skill in the art will recognize that an increase in starting temperature may accelerate the reaction whereas a decrease in initial temperature may slow the reaction rate, either of which may be desirable for particular applications.

In some embodiments, irradiation is carried out in a manner that results in the complete conversion of GO to graphene. However, this is not always the case. In some embodiments, one or more of the amount, duration, intensity and wavelength(s) of irradiation is adjusted or tuned so as to cause only partial deoxygenation of the GO, but not complete conversion to graphene. The result may be the partial deoxygenation of the GO, or the substantially complete dexoygenation of GO, producing graphene. In other words, as those of skill in the art will recognize, the deoxygenation of GO to graphene need not be an "all or nothing" event. To be "substantially complete" usually at least about 75%, 80%, 85%, 90%, 95%, 99%, or even up to about 100% of the GO is converted to graphene.

The progress of the reaction may be monitored by any suitable method, examples of which include but are not limited to UV-VIS spectral data, FTIR, Raman spectroscopy, etc.

Once the reaction has proceeded sufficiently, the source of radiation is withdrawn or removed and the graphene sheets are removed from the reaction mixture. For example, the solution may be centrifuged and the graphene separated after centrifuging, or the solution may be filtered to separate the graphene sheets, etc. The graphene may be rinsed (e.g. with water or another solvent, e.g. an alcohol), dried and stored for further use.

The production of metal-graphene nanocomposites may be carried out generally using the same procedure as that which is described above for the production of graphene. However, in this embodiment, what is irradiated is a mixture of GO plus at least one metal of interest. Generally, when the GO is dispersed in a liquid solution, soluble metal salts are used. In the presence of metal ions, upon exposure to microwave energy as described herein, simultaneous reduction of the GO and metal ions takes place and metal-graphene nanocomposites are formed.

Examples of metals that may be used include but are not limited to Pd, Co, Au, Ag, Cu, Pt, Ni, Fe, Mn, Cr, V, Ti, Sc, etc and rare earth metals such as Ce, Pr, Nd, Sm, Gd, Hom Er, Yb, etc., and other metals such as Al, Ga, Sn, Pb, In, Mg, Ca, Sr, Na, K, Rb, Cs, etc. Also, semiconductors can be used such as Si, Ge, CdSe, CdS, CdTe, ZnO, ZnS, ZnSe, etc. Generally, the metals are provided as salts, i.e. with a negative counterion such as $Cl^-$, $NO_3^-$, sulfate, chlorate, borate, acetate, etc. In some embodiments, two or more metals are included, i.e. the resulting catalyst is bi-metallic (or tri-metallic, etc., depending on how many metals are present). Exemplary combinations of metals include but are not limited to: Pd plus Co; Au plus Ag, Pd plus Pt, Cu plus Pd, Pt plus Fe, etc.

The metals in the mixture that is irradiated are generally in the form of e.g. metal salts, and the concentration of the metal ions is generally in the range of from about 1% to about 20-30%, depending on, for example, the desired density of metal on the graphene sheet that is formed.

In another embodiment, semiconductor materials mixed with and irradiated with the GO and graphene sheets with associated semiconductor particles are formed. Examples of such substances include but are not limited to silicon, titanium and zinc oxides, CdSe, ZnS, CdS, etc. The conditions for carrying out such reactions are generally the same as those for the simultaneous reduction of GO and metal ions as described above. When Si is used, the concentration of Si in the mixture that is irradiated is generally from about 1% to about 20%, and the Si is generally in the form of Silicon powder or Si nanoparticles. Similar concentrations are used for the other semiconductor materials. Further, in some embodiments, semiconductor materials may be reduced together with GO and one or more metals of interest as described above.

Graphene Synthesis Via Microwave Irradiation of Solid Reactants Under Microwave Plasma Condition In contrast, to solution methods, in another embodiment, graphene is produced by microwave irradiation of solid graphite oxide without the use of a solvent or chemical reducing or capping agents. The present methods thus advantageously eliminate the need for the use of potentially toxic and/or costly reducing agents and solvents, thereby providing a "green", environmentally sound method for producing graphene. Further, no heat/energy source is required other than microwaves, which are readily available to those of skill in the art and economical to generate.

The methods generally involve providing solid graphite oxide (GO) and exposing the solid GO to microwave radiation, i.e. irradiating the GO with microwaves. Those of skill in the art are familiar with commercial sources of solid GO, and alternatively, are also familiar with methods of synthesizing solid GO.

Generally, prior to exposing the GO to microwave energy, the GO is exfoliated in order to separate the layers. This is generally accomplished by dispersing GO in water using ultrasound or stirring until a clear well-dispersed solution is obtained with a golden yellow color. Thereafter, the exfoliated GO is dried prior to use.

Exposure to microwave energy in the range of e.g. from about 0.7 GH to about 24 GHz in wavelength is usually carried out for a period of time sufficient to catalyze the conversion to graphene, although wider ranges of energy or narrower ranges of may also be used. In some embodiments, the energy levels are, for example, about 0.9 to about 2.4 GHz. Those of skill in the art will recognize that the length of time required for the reaction to occur will depend on several factors, e.g. the amount of GO being reacted, the temperature of the reaction, the power of the microwaves that are employed, the presence or absence of other materials (e.g. metals, see below) being incorporated into the graphene, etc.

The length of exposure of GO to microwave energy will vary depending on the wavelength and strength of radiation that is used and the amount of GO that is irradiated. Generally, these variables are adjusted so that the time of radiation is in the range of from about 10 seconds to about 10 minutes, i.e. about 10, 20, 30, 40, 50, or 60 seconds, or 1, 2, 3, 4, 5, 6, 7, 8, 9, or 10 minutes, depending on the microwave power and the amount of graphene oxide. However, longer times (e.g. 15, 20, 25 or 30 minutes or more) may be utilized, if required to produce the desired end result. Further, several cycles of irradiation may be used, e.g. from about 1 to about 10 or more cycles (i.e. about 1, 2, 3, 4, 5, 6, 7, 8, 9, or 10 cycles) with each cycle including an exposure of the GO to the source of radiation of at least about one minute or more, as described above. As those of ordinary skill in the art will readily recognize, optimization of reaction conditions for a particular system may be carried out by monitoring the resulting graphene, e.g. by UV-VIS spectral data, FTIR, Raman spectroscopy, AFM, TEM, XRD, etc. and adjusting conditions accordingly.

In some embodiments, irradiation is carried out in a manner that results in the complete conversion of GO to graphene. However, this is not always the case. In some embodiments, one or more of the amount, duration, intensity and wavelength(s) of irradiation is adjusted or tuned so as to cause only partial deoxygenation of the GO, but not complete conversion to graphene. The result may be the partial deoxygenation of the GO, or the substantially complete dexoygenation of GO, producing graphene. In other words, as those of skill in the art will recognize, the deoxygenation of GO to graphene need not be an "all or nothing" event. To be "substantially complete" usually at least about 75%, 80%, 85%, 90%, 95%, 99%, or even up to about 100% of the GO is converted to graphene.

Once the reaction has proceeded sufficiently and the source of microwave radiation is withdrawn or removed, the graphene sheets may be, for example, rinsed (e.g. with water or another solvent, e.g. an alcohol), dried and stored for further use.

The solid and liquid phase methods of the invention permit the facile production of high quality graphene (e.g. graphene sheets) for many applications, examples of which include but are not limited to electronics, circuits (e.g. integrated circuits), various devices such as diagnostic and detection devices; in transistors; in capacitors (e.g. ultracapacitors); as antibacterials; in the building of ultra-light structures; etc. The sheets may be used as is (i.e. in the form of two-dimensional "sheets"), or, alternatively, sheets made according to the invention may be used to form other structures.

The methods of the invention also encompass the simultaneous reduction of solid graphite oxide and one or more solid metal salts, resulting in the dispersion of metallic and/or multi-metallic (e.g. bi-metallic, tri-metallic, etc.) nanoparticles supported on the large surface area of a thermally stable 2D graphene sheet. Further, nanoparticles may be supported which convey semiconductor properties to the graphene. While such constructs may be used for any of a wide variety of applications (including those described above for graphene sheets), in one embodiment, such constructs are used as metallic catalysts. It has been surprisingly and unexpectedly discovered that metallic catalysts supported on graphene which are produced by microwave irradiation display significantly superior catalytic properties compared to catalysts with similar compositions, but made by other methods. For example, the exemplary catalyst palladium (described below), when supported on graphene sheets, provides catalytic capabilities that are vastly superior to those achieved heretofore using prior art Pd catalysts. Such metallic catalysts may be used in a variety of settings, e.g. for the manufacture of substances of interest, and are of special interest to the pharmaceutical industry, e.g. for use in catalyzing a variety of chemical reactions and transformations, particularly at high temperature. The use of such catalysts permits rapid and economical synthesis of substances of interest, e.g. drugs, or substances used in the manufacture of drugs. Further, the catalysts described herein are highly recyclable; repeated use of a Pd/G catalyst in a Suzuki cross-coupling reaction resulted in quantitative yield of product for up to at least 8 cycles (see Example 3). Further uses of the metal catalysts described herein include but are not limited to: catalysis reactions, various cross- and homo-coupling reactions, use in Fischer-Tropsch Synthesis, Buchwald-Hartwig amine synthesis, hydrogen production reactions, CO oxidation, etc., as well as for use as or in sensors, hydrogen storage, energy conversion, and for other applications.

In order to implement this aspect of the invention, solid metal powder or nanoparticles (e.g. one or more solid metal salts) is/are mixed with solid GO and exposed to microwave irradiation, as described above for graphene sheets. In one embodiment, metal powder or nanoparticles is/are mixed with GO to form a mixture that is, e.g. pressed into a pellet (cake, block, layer, sheet, etc.) using high pressure. The mixed pellet is then exposed to microwaves as described above, and metal-graphene nanocomposites are formed. In the final product, nanoparticles (i.e. nanoclusters, nanocrystals, etc.) of metals are attached to and supported on the sheet of graphene.

Examples of metals that may be used in the practice of the invention include but are not limited to Pd, Co, Au, Ag, Cu, Pt, Ni, Fe, Mn, Cr, V, Ti, Sc, etc. and rare earth metals such as Ce, Pr, Nd, Sm, Gd, Hom Er, Yb, etc., and also other metals such as Al, Ga, Sn, Pb, In, Mg, Ca, Sr, Na, K, Rb, Cs, etc. Also, semiconductors can be used such as Si, Ge, CdSe, CdS, CdTe, ZnO, ZnS, ZnSe, etc. Generally, the metals are provided as salts, i.e. with a negative counterion such as $Cl^-$, $NO_3^-$, sulfate, chlorate, borate, acetate, etc. In some embodiments, two or more metals are included, i.e. the resulting catalyst is bi-metallic (or tri-metallic, etc., depending on how many metals are present). Exemplary combinations of metals include but are not limited to: Pd plus Co; Au plus Ag, Pd plus Pt, Cu plus Pd, Pt plus Fe, etc.

In another embodiment, semiconductor materials mixed with and irradiated with the GO and graphene sheets with associated semiconductor particles are formed. Examples of such substances include but are not limited to silicon, titanium and zinc oxides, CdSe, ZnS, CdS, etc. The conditions for carrying out such reactions are generally the same as those for the simultaneous reduction of GO and metal ions as described above. When Si is used, it is generally in the form of silicon powder or Si nanoparticles. Similar concentrations are used for the other semiconductor materials. Further, in some embodiments, semiconductor materials may be reduced together with GO and one or more metals of interest, as described above.

The metals or semiconductor materials in the mixture that is irradiated are generally in the form of salts, and the concentration of the metal ions is generally in the range of from about 1% to about 20-30% of the total weight of the solid mixture, depending on, for example, the desired density of metal or semiconductor substance on the graphene sheet that is formed. In the final product, the weight % of metal is typically from about 1 to about 10%, e.g. about 1, 2, 3, 4, 5, 6, 7, 8, 9, or 10%, but may be more if desired.

Palladium Catalysts

As described in detail in Examples 3 and 4 below, the highest turnover rate ever observed for a Suzuki reaction has been observed using super-active, highly efficient Pd/G catalysts produced by exposure of GO and Pd salts to microwave energy. Further, with several types of reactions (e.g. Suzuki, Heck and Sonogashira reactions) quantitative or near quantitative conversion of substrates is achieved within minutes, making these catalysts vastly superior to catalysts made using conventional methods. In addition, the catalysts are recyclable, i.e. they can be used multiple times without a significant decrease in product yield.

Such Pd catalysts are synthesized from GO and Pd metal using microwave energy, and both solid and solution phase syntheses are contemplated. The preparation of Pd/G catalysts using solid GO and metal salts, as discussed herein, provides for the successful use of Pd/G catalysts produced as demonstrated.

Accordingly, the present invention provides Pd/G catalysts formed by microwave radiation of solid GO and solid Pd metal (e.g. a Pd salt) or by microwave radiation of solutions of GP and PD. In addition, the invention provides the use of Pd/G catalysts formed by microwave radiation of solid GO and solid Pd metal or by microwave radiation of GO and Pd metal in solution, as high efficiency catalysts. Pd catalysts formed from solid reactants are advantageously substantially free of residual contaminants such as residual solvent or residual reducing or capping agents, since neither is used in the reaction. Further, the invention provides methods of carrying out a quantitative or near quantitative cross-coupling reaction (e.g. a Suzuki, Heck or Sonogashira cross-coupling reaction) using a Pd/G catalyst. By "quantitative" we mean that the product yield is 100%; by "near quantitative", we mean that the product yield is at least about 65, 70, 75, 80, 85, 90, 91, 92, 93, 94, 95, 96, 97, 98, or 99%, or even higher. Further, the turnover number for reactions using the super-efficient Pd/G catalysts described herein are in the range of at least about 25,000; 30,000; 35,000; 40,000; 45,000; 50,000; 55,000; 60,000; 65,000; 70,000; 75,000; 80,000; 85,000; 90,000; 95,000; 100,000; 105,000 $h^{-1}$, or higher. A further characteristic and advantage of these Pd/G catalysts is that they can be used for multiple rounds of reaction before product yields begin to wane. For example, the Pd/G catalysts made by using microwave energy (both solid and solution methods) may be used at least 2, 3, 4, 5, 6, 7, 8, 9, 10 or even more times. Typically, the catalysts maintain quantitative or near quantitative yields for at least 5 cycles.

The invention further provides a method of catalyzing chemical coupling of at least two reactants of interest. The method comprises the steps of 1) providing a Pd catalyst comprising nanoparticulate Pd supported on graphene, the Pd catalyst having been produced by irradiating a mixture of graphite oxide (GO) and Pd metal with microwave radiation; and 2) combining the at least two reactants of interest in the presence of the Pd catalyst and under conditions which allow the Pd catalyst to catalyze the chemical coupling of the at least two reactants of interest. Those of skill in the art will recognize that conditions which allow the Pd catalyst to catalyze the reaction may include, for example, carrying out the reaction in a suitable solvent and in a suitable container at an appropriate temperature, providing additional factors, etc. Those of skill in the art will comprehend that, in some embodiments, factors that may be varied while still practicing the claimed invention within the intended spirit and scope include but are not limited to factors such as solvents conditions, the use of alternative bases, the time of reaction, the energy source (e.g. use of an alternative energy sources such as traditional thermal heat, radiant energy, etc. instead of or in addition to microwaves), etc.

The Pd catalysts used in the reaction are preferably "recyclable", i.e. the catalyst can be used repeatedly for multiple rounds of reactions without losing its ability to catalyze the reaction and provide high product yields. In fact, product yields for the reaction are typically very high (e.g. at least about 65%) but can be much higher (e.g. about 70, 75, 80, 85, 90, 95, 96, 97, 98, 99 or 100%), and these high levels of yield are generally maintained for at least 5 coupling cycles, and frequently for more than 5 cycles, e.g. for 6, 7, 8, 9, 10, 11, 12, or more cycles. Thus, Pd catalysts as described herein use highly efficient ("super-efficient") and display very high levels of catalytic activity ("super-active"). Use of these Pd catalysts is thus expeditious and economically advantageous. In fact, these same properties generally apply to all catalysts described herein, e.g. catalysts formed using other metals as listed above.

The Pd (and other) catalysts described herein may be used to catalyze a variety of chemical reactions, especially chemical coupling reactions such as cross-coupling. Exemplary reactions include but are not limited to Suzuki cross-coupling reactions, Heck cross-coupling reaction, Sonogashira cross-coupling reactions, Negish reactions, Stille reactions, Buchwalk-Hartwig reactions, and others that will occur to those of skill in the art as amenable to catalysis using the catalysts of the invention. In one embodiment, the chemical coupling is a Suzuki cross-coupling reaction. For Suzuki reactions, the Pd catalysts described herein surprisingly and unexpectedly display a turnover frequency greater than 100,000 h$^1$ (e.g. upwards of 108,000 h$^1$) and product yields of at least 65%. Depending on the substrates involves, product yields can be much higher, e.g. over 80%, or in some cases 90% or even greater (e.g. 95%, see Example 3).

In other embodiments, the chemical coupling is a Heck cross-coupling reaction. For this reaction, the product yield is generally at least 84% and in some cases is near 100% (see Example 3).

In yet other embodiments, the chemical coupling is a Sonogashira cross-coupling reaction, the product yields for which are generally at least 88%, but may be considerably higher, e.g. approaching 100%.

In one embodiment of the method, the Pd catalyst is prepared by irradiating solid GO and solid Pd with microwave radiation, and the Pd catalyst that is formed is substantially free of residual contaminants (e.g. residual solvent, residual reducing agents, residual capping agents etc.) since other substances are not used when making the catalyst.

EXAMPLES

Example 1

Methods for the Production Nanoparticle Catalysts Supported on Graphene by Microwave Irradiation of Solids An exemplary protocol for the preparation of metallic nanoparticles supported on 2-dimensional graphene sheets is as follows:
1. 200 mg graphene oxide+2% metal precursor+30 mL water
2. Sonicate for one hour at room temperature
3. Stir overnight (room temperature)
4. Dry at 80° C.
5. Measure XRD of the solid before MWI
6. Microwave Irradiation (MWI) of the solid for 10 seconds to 5 minutes.
7. Measure XRD of the solid after MWI The "metal precursor" that is employed is typically a metal salt. Metal salts which were employed in this Example were: Fe(NO$_3$) 3.9H; Cu(NO$_3$) 2.2.5H; Ni(NO$_3$) 2.6H; Ag(NO$_3$); Co(NO$_3$) 2.6H; and Pd(NO$_3$)$_2$. TEMs of the metallic nanoparticles supported graphene sheets that were produced are depicted in FIGS. 3A-F and 4A and B.

Example 2

Microwave-Assisted Synthesis of Palladium Nanoparticles Supported on Graphene: a Highly Active and Recyclable Catalyst for Carbon-Carbon Cross-Coupling Reactions We have developed an efficient method to generate highly active Pd nanoparticles supported on graphene (Pd/G) by microwave-assisted chemical reduction of the corresponding aqueous mixture of a palladium salt and dispersed graphite oxide (GO) sheets. The Pd/G demonstrated excellent catalytic activity for the carbon-carbon cross-coupling reactions (Suzuki, and Heck) with a broad range of utility under ligand-free ambient conditions in an environmentally friendly solvent system. It also offers a remarkable turnover frequency (108,000 h$^{-1}$) observed in the microwave-assisted Suzuki cross-coupling reactions with easy removal from the reaction mixture, recyclability with no loss of activity, and significantly better performance than the well-known commercial Pd/C catalyst. The catalyst was fully characterized by a variety of spectroscopic techniques including X-ray diffraction (XRD), Raman, TGA, electron microscopy (SEM, TEM), and X-ray photoelectron spectroscopy (XPS). The remarkable reactivity of the Pd/G catalyst toward Suzuki cross-coupling reactions is attributed to the high degree of the dispersion and concentration of Pd(0) nanoparticles supported on graphene sheets with small particle size of 7-9 nm due to an efficient microwave-assisted reduction method.

INTRODUCTION

Graphene's unique hexagonal atomic layer structure and unusual properties, including the highest electron mobility of all known materials at room temperature, has motivated the development of new composite materials for nanoelectronics, supercapacitors, batteries, photovoltaics, and related devices [1-11]. However, other properties of graphene such as high thermal, chemical, and mechanical stability as well as high surface area also represent desirable characteristics as 2D support layers for metallic and bimetallic nanoparticles in heterogeneous catalysis, fuel cells, chemical sensors, and hydrogen storage applications [12-23]. Recent advances in the production of graphene sheets through the reduction of exfoliated graphite oxide (GO) have provided efficient approaches for the large-scale production of chemically converted graphene (CCG) sheets, which can be readily used as a catalyst support [24-28]. One of the catalytic applications in which graphene support may provide some significant advantages is in the area of cross-coupling chemistry [29,30]. Palladium-catalyzed cross-coupling reactions have been of strategic importance in organic synthesis since their discovery in the 1970s [29-33]. These reactions have been extensively used for the assembly of complex organic molecules for a wide variety of applications with considerable impact on the chemical and pharmaceutical industries [29-33]. Due to their broad applicability for C—C bond formation, enormous interest continues in this area with more focus directed toward developing more efficient and recyclable catalysts that allow for industrial applications within environmentally benign processes.

Cross-coupling reactions have typically been performed under homogeneous conditions employing a ligand to enhance the catalytic activity and selectivity for specific reactions [29-33]. However, the issues associated with homogeneous catalysis remain a challenge to pharmaceutical applications of these synthetic tools due to the lack of recyclability and potential contamination from residual metals in the reaction product [34,35]. In order to address this issue, a significant effort has been made to advance the development of cross-coupling catalysts where the palladium is fixed to a solid support such as activated carbon [36,37], zeolites [38, 39], polymers [40,41], or nanoparticles [42-46]. Although heterogeneous supports allow efficient recycling, a decrease in the activity of the immobilized catalysts is frequently observed [47,48]. Therefore, the development of heterogeneous Pd nanocatalysts that combine high activity, stability, and recyclability is an important goal of nanomaterials research that is likely to have a considerable impact on the chemical and pharmaceutical industries in the future.

Only recently have graphene (G) and graphite oxide (GO) been considered as potential support systems for palladium-catalyzed C—C coupling applications [49]. Because of the higher specific surface area (1500 m$^2$/g, theoretical value 2600 m$^2$/g)$^2$ and thermal stability of graphene when compared to graphite oxide (surface area 200-400 m$^2$/g), G-based nanocatalysts might be expected to exhibit superior activity compared to GO-based catalysts [5,6]. We hypothesized that the preparation of these materials may play a critical role in the catalytic activity for specific synthetic applications. For this reason, we chose to evaluate the cross-coupling activity of Pd/G nanomaterials prepared using microwave radiation. In this paper, we report on the excellent catalytic activity and stability of palladium nanoparticles supported on graphene (Pd/G) as a catalyst for both Suzuki and Heck C—C coupling reactions. Furthermore, we have obtained valuable insights from X-ray photoelectron spectroscopy (XPS) studies into the critical parameters that affect heterogeneous cross-coupling catalytic activity in these specific applications. This work provides a significant step toward the development of clean technologies for organic synthesis.

In the present work, the Pd/G nanocatalysts were prepared using the recently reported microwave irradiation (MWI) method [28]. MWI has been demonstrated for the synthesis of a variety of nanomaterials including metals, metal oxides, bimetallic alloys, and semiconductors with controlled size and shape without the need for high temperature or high pressure [50-54]. The main advantage of MWI over other conventional heating methods is that the reaction mixture is heated uniformly and rapidly. This has been demonstrated for the acceleration of homogeneous catalysis in organic synthesis [55]. Due to the difference in the solvent and reactant dielectric constants, selective dielectric heating can provide significant enhancement in the transfer of energy directly to the reactants, which causes an instantaneous internal temperature rise [55]. This temperature rise in the presence of hydrazine hydrate as a reducing agent has provided a facile and efficient method by which palladium ions and GO can be effectively reduced into a dispersion of metallic nanoparticles supported on the large surface area of the graphene sheets. The reduction of GO by hydrazine hydrate under MWI proceeds by rapid deoxygenation of GO to create C—C and C=C bonds [24-28]. Unlike conventional thermal heating, MWI allows better control of the extent of GO reduction by hydrazine hydrates as both the MWI power and time can be adjusted to yield a nearly complete concurrent reduction of GO and the palladium salt. In contrast, the corresponding palladium supported on graphite oxide sheets (Pd/GO) catalyst was prepared by the microwave-assisted deposition of palladium nitrate in a GO dispersion without the addition of hydrazine hydrate. In this case, the temperature rise during MWI causes subsequent supersaturation and nucleation to form Pd nanoparticles supported on the GO sheets.

2. EXPERIMENTAL

2.1. Materials and Methods

High-purity graphite powder (99.9999%, 200 mesh) was purchased from Alfa Aesar. Palladium nitrate (10 wt. % in 10 wt. % $HNO_3$, 99.999%) and hydrazine hydrate were obtained from Sigma Aldrich. Aryl bromide and chloride, potassium carbonate, arylsubstituted boronic acid, and olefins were also purchased from Aldrich and used as received. A mixture of ethanol/deionized water was used for the Suzuki and Heck cross-coupling reactions.

TEM images were obtained using a JEOL JEM-1230 electron microscope operated at 120 kV equipped with a Gatan UltraScan 4000SP 4 K×4 K CCD camera. Samples for TEM were prepared by placing a droplet of a colloid suspension in toluene on a Formvar carbon-coated, 300-mesh copper grid (Ted Pella) and allowed to evaporate in air at room temperature. The small-angle X-ray diffraction (SA-XRD) patterns were measured at room temperature with an X'Pert Philips Materials Research Diffractometer using the Cu KaR radiation. Scanning electron microscopy (SEM) and energy-dispersive X-ray spectroscopy (EDS) were carried out using a Quantum DS-130S Dual Stage Electron Microscope. The morphology of the graphene sheets was examined by an atomic force microscope (Nano-Scope Ma, Digital Instruments) using tapping mode. The thermal gravimetric analysis was carried out on a TGA Q5000 from TA instruments. The Raman spectra were measured using an excitation wavelength of 457.9 nm provided by a Spectra-Physics model 2025 argon ion laser. The laser beam was focused to a 0.10-mm-diameter spot on the sample with a laser power of 1 mW. The samples were pressed into a depression at the end of a 3-mm-diameter stainless steel rod, held at a 30 degree angle in the path of the laser beam. The detector was a Princeton Instruments 1340×400 liquid nitrogen CCD detector, attached to a Spex model 1870 0.5 meter single spectrograph with interchangeable 1200 and 600 lines/mm holographic gratings (Jobin-Yvon). The Raman scattered light was collected by a Canon 50 mm f/0.95 camera lens. Though the holographic gratings provided high discrimination, Schott and Corning glass cut-off filters were used to provide additional filtering of reflected laser light, when necessary. The X-ray photoelectron spectroscopy (XPS) analysis was performed on a Thermo Fisher Scientific ESCALAB 250 using a monochromatic Al KR X-ray. GC-MS analyses were performed on Agilent 6890 gas chromatograph equipped with an Agilent 5973 mass selective detector. A CEM Discover microwave instrument was used for cross-coupling reactions. The reactions were performed at operator selectable power output of 250 W. $^1H$ and $^{13}C$ NMR were acquired on a Mercury 300 MHz spectrometer. High-resolution mass spectrometry analyses were obtained from the Virginia Commonwealth University mass spectrometry facilities.

2.2. Synthesis of Pd/G and Pd/GO Nanoparticles

In the experiments, GO was prepared by the oxidation of high purity graphite powder (99.9999%, 200 mesh) with $H_2SO_4/KMnO_4$ according to the method of Hummers and Offeman [56]. After repeated washing of the resulting yellowish-brown cake with hot water, the powder was dried at room temperature under vacuum overnight. For the preparation of Pd/G, 0.1 g of the dried GO and an appropriate amount of palladium nitrate (10 wt. % in 10 wt. % $HNO_3$, 99.999%) were sonicated in deionized water until a homogeneous yellow dispersion was obtained. The solution was placed inside a conventional microwave after adding 100 µl of the reducing agent hydrazine hydrate (HH). The microwave oven (Emerson MW8119SB) was then operated at full power (1000 W), 2.45 GHz, in 30-s cycles (on for 10 s, off and stirring for 20 s) for a total reaction time of 60 s. The yellow solution of Pd nitrate-GO changed to a black color, indicating the completion of the chemical reduction to graphene. The Pd/G sheets were separated by using an Eppendorf 5804 centrifuge operated at 5000 rpm for 15 min and dried overnight under vacuum. The same method was also used for the preparation of Pd/GO except that no HH was added during the MWI.

2.3. General Procedure for Suzuki Reactions

Figure 15:
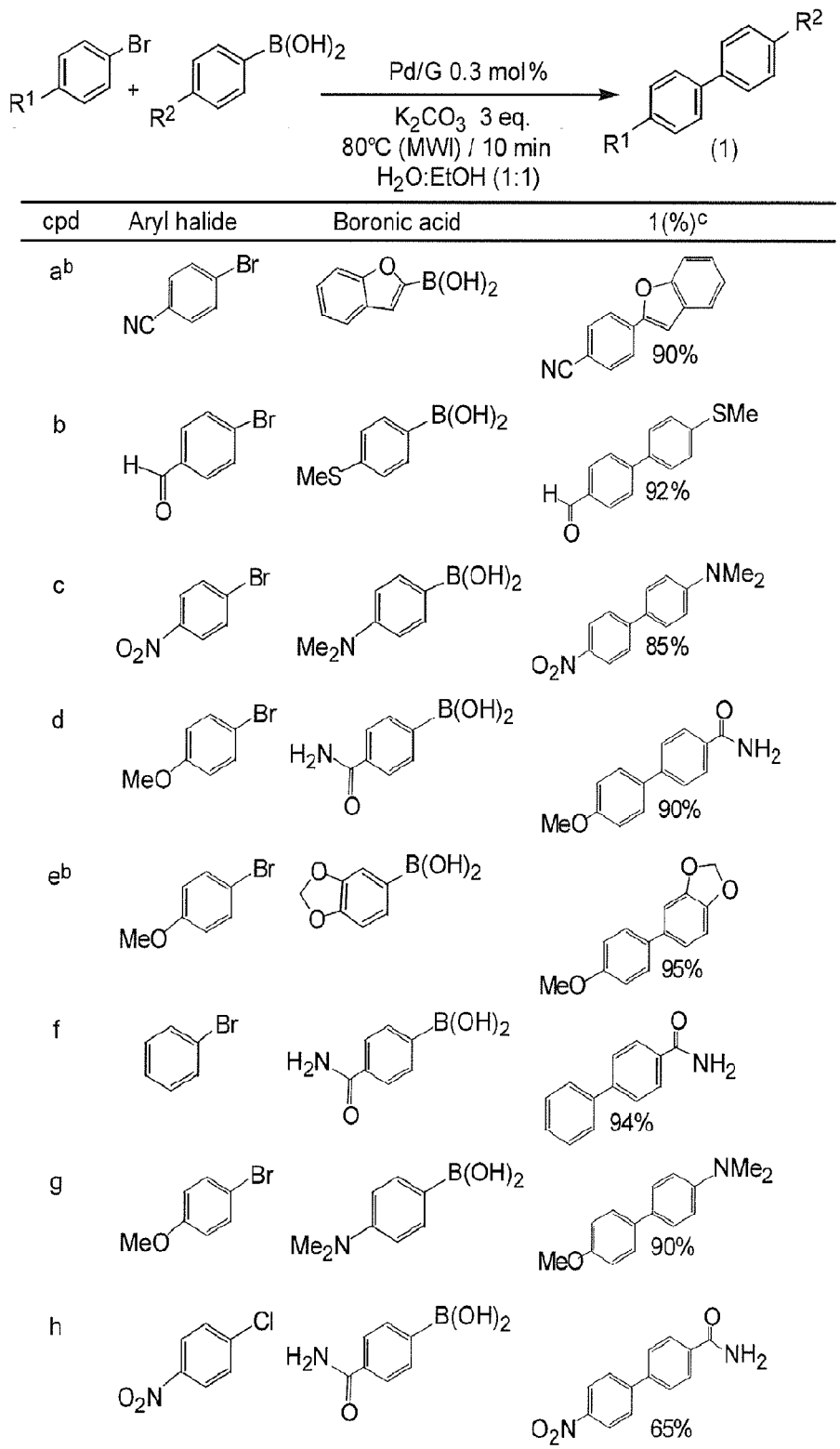
FIG. 15. Evaluation of catalysts for Suzuki cross-coupling. a=aryl halide (0.51 mmol), boronic acid (0.61 mmol, 1.2 eq.), potassium carbonate (212 mg, 1.53 mmol, 3 eq.), and Pd/G (2.1 mg, 1.53 mmol, 0.3 mol %) in 8 mL ($H_2O$:EtOH) (1:1) were heated at 80° C. (MWI) for 10 min. b=Reactions were completed at r.t. after 30 min. c=Isolated yields.

Aryl bromide (0.51 mmol, 1 eq.) was dissolved in a mixture of 8 mL H2O:EtOH (1:1) and placed in a 35-mL microwave tube. To this were added the aryl boronic acid (0.61 mmol, 1.2 eq.) and potassium carbonate (1.53 mmol, 3 eq.). Palladium on graphene nanoparticles (Pd/G) (2.1 mg, 1.53 mmol, 0.3 mol %) were then added, and the tube was sealed and heated under microwave irradiation (250 W, 2.45 MHz) at the certain temperature and time which is indicated in FIG. 15. Upon the completion of the reaction period, the reaction mixture was diluted with 20 mL of $H_2O$ and extracted with $CH_2Cl_2$ (3×50 mL). The organic layers were combined, dried over anhydrous Na$_2$SO$_4$, and filtered. The solvent in the filtrate was then removed in vacuo to give a solid. The pure products were obtained by flash chromatography using hexane:ethyl acetate as the eluent or by washing the solid products with an appropriate non-polar solvent such as hexanes followed by decanting the hexanes layer.

2.4. General Procedure for the Heck Coupling

Aryl bromide (0.51 mmol, 1 eq.) was dissolved in a mixture of 8 mL H$_2$O; EtOH (1:1) and placed in a 35-mL microwave tube. To this were added the corresponding alkene (1.02 mmol, 2 eq.) and potassium carbonate (1.53 mmol, 3 eq.). Palladium on graphene nanoparticles (Pd/G) (2.1 mg, 1.53 µmol, 0.3 mol %) were then added; the tube was sealed and heated under microwave irradiation (250 W, 2.45 MHz) at 150° C., for 10 min. Upon the completion of microwave heating, the reaction mixture was extracted with CH$_2$Cl$_2$ (3×50 mL). The organic layers were combined, dried over anhydrous Na$_2$SO$_4$, and filtered. The solvent in the filtrate was then removed in vacuo to give a solid. The pure products were obtained by flash chromatography using hexane:ethyl acetate as the eluent or by washing the solid products with an appropriate non-polar solvent such as hexanes followed by decanting the hexanes layer.

2.5. Procedure for Recycling the Catalysts

Bromobenzene (50 mg, 0.32 mmol, 1 eq.) was dissolved in a mixture of 4 mL H$_2$O:EtOH (1:1) and placed in a 10-mL microwave tube. To this were added phenyl boronic acid (47 mg, 0.382 mmol, 1.2 eq.) and potassium carbonate (133 mg, 0.96 mmol, 3 eq.). Palladium catalyst (1.3 mg, 0.96 lmol, 0.3 mol %) was then added; the tube was sealed and heated at 80° C. for 5 min under microwave irradiation (250 W, 2.45 MHz). The progress of the reaction was monitored by GC-MS analysis. After the completion of the reaction, the mixture was diluted with 10 mL of EtOH and shaken. The entire mixture was centrifuged and the solvent above the Pd nanoparticle catalyst was completely decanted. EtOH washing followed by centrifugation was repeated two additional times to assure the removal of all products from the catalyst surface. The Pd nanoparticle catalyst was then directly transferred to another microwave tube along with fresh reagents for the next run. This procedure was repeated for every run, and the percent conversion of product was determined by the means of GC-MS spectroscopy.

Figure 12:
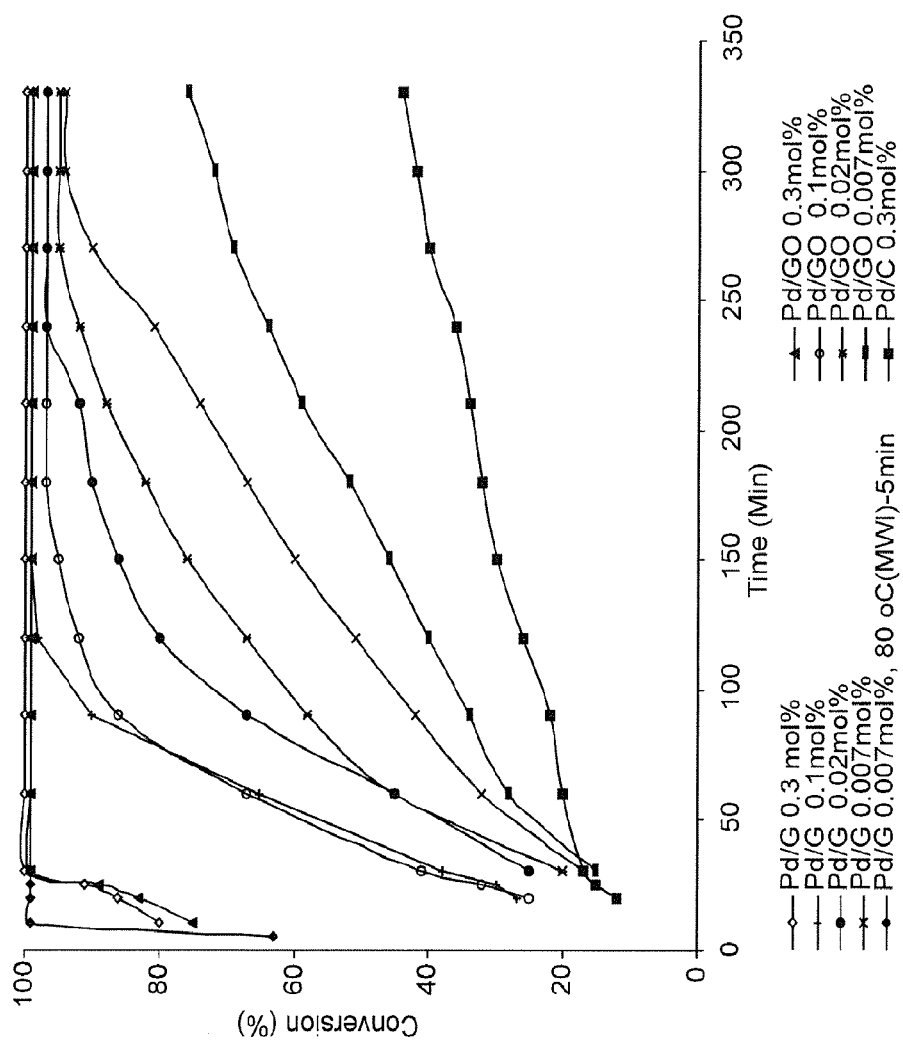
FIG. 12. Effect of catalyst concentrations for the Pd/G and Pd/GO on the conversion of reaction (FIG. 11B).

2.6. Procedure for Catalyst Concentration Effects (FIG. 12)

Bromobenzene (50 mg, 0.32 mmol, 1 eq.) was dissolved in a mixture of 4 mL H$_2$O:EtOH (1:1) and placed in a 10-mL microwave tube. To this were added phenyl boronic acid (47 mg, 0.382 mmol, 1.2 eq.) and potassium carbonate (133 mg, 096 mmol, 3 eq.). Palladium catalysts nanoparticles (X mmol, Y mol % as indicated in FIG. 12), were then added, and the tube was sealed and stirred at room temperature (r.t.). An aliquot of the reaction mixtures was taken after 30, 60, 120, 180, 240, 300, and 360 min, diluted with 10 mL of CH$_3$CN, and injected into the GC/MS. The percent conversions of the products were then calculated based on the consumption of bromobenzene starting materials by means of GC-MS spectroscopy.

Figure 7A:
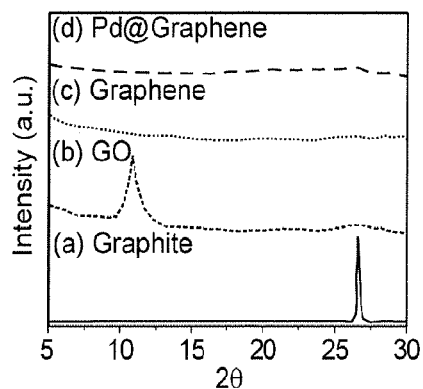
FIGS. 7A and B. (a) Small-angle XRD patterns of graphite, GO, graphene, and Pd/graphene (Pd/G) samples. (b) Small-angle XRD pattern of Pd/graphite oxide (Pd/GO) prepared by MWI of a mixture of GO and Pd nitrate solution in water without the addition of hydrazine hydrate.
Figure 7B:
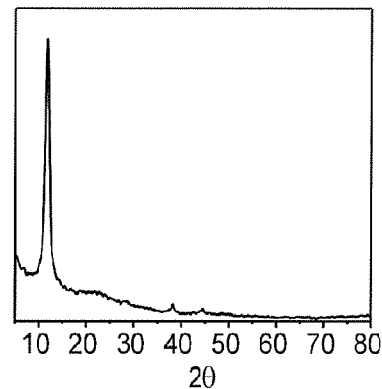

3. RESULTS AND DISCUSSION 3.1. Characterization of the Pd/G and Pd/GO Nanoparticle Catalysts Characterization of the graphene samples prepared by the HHMWI method was examined in detail using EDS, XPS, TEM, and AFM analyses (not shown). Here, we focus on the characterization and catalytic activity of the Pd/G and Pd/GO nanocatalysts. FIG. 7A displays the XRD patterns of the initial graphite powder, the prepared GO, and the chemically converted graphene and Pd/G prepared by the HH-MWI method. The initial graphite powder shows the typical sharp diffraction peak at 2θ=26.7° with the corresponding d-spacing of 3.34 Å. The exfoliated GO sample shows no diffraction peaks from the parental graphite material and only a new broad peak at 2θ=10.9° with a d-spacing of 8.14 Å observed. This indicates that the distance between the carbon sheets has increased due to the insertion of interplaner oxygen functional groups [24-28]. After MWI of the GO in the presence of HH as the reducing agent, the XRD of the resulting graphene shows the disappearance of the 10.9° peak confirming the complete reduction of the GO sheets [24-28]. A similar XRD spectrum is observed for the Pd/G sample prepared by the simultaneous reduction of GO and palladium nitrate using HH under MWI. The very small broad peak around 2θ=26.7° in the Pd/G sample could suggest the presence of a minor component of multilayer graphene. The presence of Pd nanoparticles could enhance the interaction among a few graphene layers. However, the very weak intensity of the 2θ=26.7° peak indicates that the extent of multilayer graphene in the Pd/G sample is insignificant.

Figure 8A:
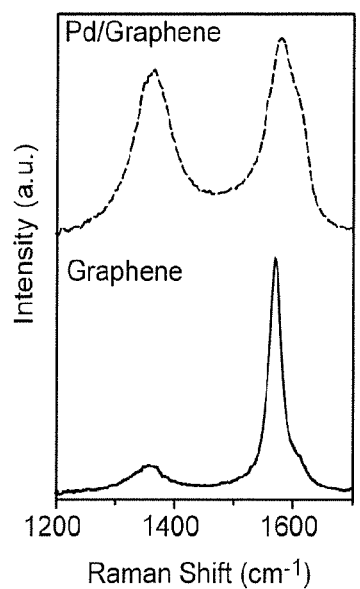
FIGS. 8A and B. (a) Raman spectra of the graphene and Pd/G samples prepared by the hydrazine hydrate (HH) MWI method in the G- and D-regions and (b) in the 2D-region.
Figure 8B:
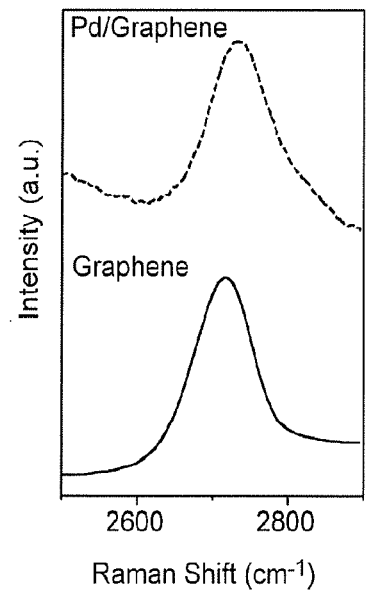

The Raman spectrum of graphene is characterized by three main features: the G mode arising from emission of zone-center optical phonons (usually observed at ~1575 cm$^{-1}$), the D mode arising from the doubly resonant disorder-induced mode (~1350 cm$^{-1}$), and the symmetry-allowed 2D overtone mode (~2700 cm$^{-1}$) [24-28,57-59]. FIG. 8 compares the Raman spectra of graphene and Pd/G samples prepared by the HH-MWI method. The spectra of graphene and Pd/G show strong G-bands at 1571 cm$^{-1}$ and 1580 cm$^{-1}$, respectively. In both cases, the G-band is redshifted from the G-band in GO (1594 cm$^{-1}$). However, the G-band of Pd/G is significantly broad and blueshifted with respect to graphene, which could be attributed to the presence of isolated double bonds that resonate at higher frequencies than the G-band of graphene [58,59]. The D-band in Pd/G at 1365 cm$^{-1}$ is significantly stronger and broader than the D-band in graphene. The D-band in graphene at 1357 cm$^{-1}$ and the D'-shoulder at 1616 cm$^{-1}$ have been attributed to structural disorder at defect sites and finite size effects, respectively [57-59]. The intensity ratio of the D-band to the G-band is used as a measure of quality of the graphitic structures since for highly ordered pyrolytic graphite; this ratio approaches zero [57-59]. As shown in FIG. 8A, the graphene sample exhibits a weak disorder-induced D-band with the D-G intensity ratio of only 0.10-0.12, thus indicating the high quality of the graphene sheets prepared by the HH-MWI method. On the other hand, the presence of Pd nanoparticles appears to induce structural disorder and defects within the graphene sheets as indicated by the high intensity ratio (0.8) of the D- to G-bands in the Pd/G sample. These structural defects, although undesirable for electronic applications of graphene, could play an important role in enhancing the catalytic activity of the Pd/G nanocatalyst. We have also observed the high-energy second-order 2D-band of the graphene and Pd/G samples around 2720 cm$^{-1}$ and 2730 cm$^{-1}$, respectively, as shown in FIG. 8B. The position and shape of the 2D peak depend on the number of graphene layers, and therefore, the 2D peak can be used to distinguish between single-layer, bilayer, and few layer graphene (FLG) [57-59]. For example, it has been shown that sheets with more than five layers have broad 2D peaks significantly shifted to positions greater than 2700 cm$^{-1}$ [57]. Based on these interpretations, we can estimate the number of layers in the graphene and Pd/G samples as 5-7 and 7-9, respectively.

The morphology of the Pd/G catalyst consists of platelets and extended sheets of lateral dimensions ranging from a few micrometers to tens of micrometers in length with layered structures as shown in the SEM image displayed FIG. 9A. EDS analysis (FIG. 9B) clearly shows the presence of Pd in the sample and that the sample consists mainly of carbon with an insignificant amount of oxygen probably due to the presence of some unreduced oxygen functional groups. This is consistent with the EDS and XPS spectra of the reduced GO (not shown), respectively. EDS analysis of GO before and after the hydrazine hydrate reduction under MWI shows that the oxygen content drops from 15.2% in GO to 5.2% in the chemically converted graphene, which is similar to the oxygen content measured in the Pd/G sample (FIG. 9B).

FIG. 10 displays representative TEM images of the Pd/G (A) and Pd/GO (B) catalysts. The palladium content in both catalysts was determined by means of inductively coupled plasma equipped with mass spectrometry (ICP-MS) and amounted to be 7.9 wt. % and 6.4 wt. %, respectively. The TEM images show the presence of uniform well-dispersed Pd nanoparticles on both G and GO sheets over very large areas of several microns (not shown). However, the nanoparticles supported on graphene appear to be smaller than those supported on the GO sheets. From multiple samples, we can estimate the average particle sizes of the Pd nanoparticles supported on G and GO to range from about 7-9 and about 12-15 nm, respectively. It also appears that there is more agglomeration of the Pd nanoparticles on GO than on G. From the statistical analysis of several TEM images, the mean sizes of the Pd nanoparticles dispersed on G and GO are found to be 8 and 14 nm, respectively, consistent with the estimation of the average particle size. It should be noted that one of the important features of our catalyst preparation is the production of large graphene sheets (several microns) homogenously decorated with well-dispersed Pd nanoparticles as shown in the TEM images (not shown).

The XPS data of the as-prepared Pd/GO catalyst (discussed later in Section 3.4) indicate that the Pd is substantially present as Pd (II). The agglomeration of the Pd nanoparticles on GO could be enhanced by the strong interaction between the Pd ions and the oxygen functional groups of the GO. Also, the slow deposition of the Pd ions in the absence of a reducing agent during MWI could result in lower supersaturation and lower nucleation rates which result in larger particle sizes [53,54]

Figure 11A:
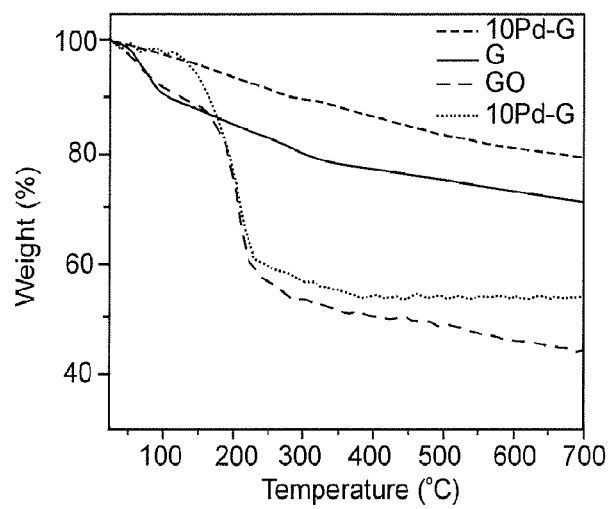
FIGS. 11A and B. A, Comparison of the TGA plots of graphite oxide (GO), graphene (G), and Pd/GO and Pd/G catalysts; B, Scheme of Suzuki cross-coupling reaction with Pd/G and Pd/GO.

We have examined the thermal stability of the prepared Pd/G and Pd/GO under a nitrogen atmosphere using thermal gravimetric analysis (TGA). As shown in FIG. 11A, the GO exhibits about 10% weight loss below 100° C. and more than 40% loss at 200° C. resulting from the removal of the labile oxygen-containing functional groups such as CO, $CO_2$, and $H_2O$ vapors [25,28]. The Pd/GO catalyst follows very much the same thermal degradation pattern as that of GO. In contrast, G and Pd/G show much higher thermal stability with much less mass loss up to 700° C. The mass loss in G and Pd/G is attributed to the presence of some oxygen functional groups since it is well known that although chemical reduction of GO results in removing most of the oxygen functional groups, a small amount of oxygen, mostly in the epoxy and ether groups, is always retained in the reduced GO [25-28]. The TGA data also suggest that the presence of Pd nanoparticles on the graphene sheets increases the thermal stability of the Pd/G catalyst. However, the mechanism of increasing the thermal stability of graphene by the Pd nanoparticles is not clearly explained at this point, and more research is needed in order to understand this effect.

3.2. Catalytic Activity Toward Suzuki Reaction

3.2.1. Effect of Catalyst Concentration

Figure 11B:
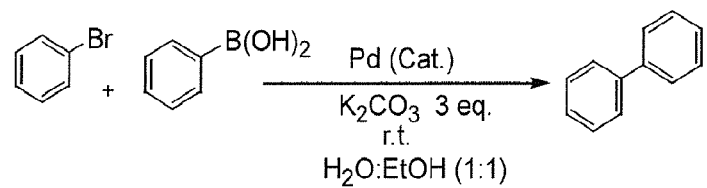

The catalytic activity of these Pd/G and Pd/GO catalysts (with Pd contents of 7.9 wt. % and 6.4 wt. %, respectively, as determined by ICP-MS) was investigated using the Suzuki cross-coupling reaction of bromobenzene and phenyl boronic acid in a mixture of $H_2O$:EtOH (1:1) at room temperature (r.t.) (FIG. 11B). FIG. 12 illustrates the % conversion of reaction in Scheme 1 for different loadings of the Pd/G and Pd/GO catalysts. While both catalysts demonstrated high activity toward Suzuki coupling, Pd/G shows slightly superior activity at lower concentrations. With 0.3 mol % loading, both catalysts show complete conversion (100%) of aryl bromide to the biphenyl product within 25 min, at room temperature (r.t.). Under the same concentration, commercially available Pd supported on activated carbon (10% Pd/C), the most often used catalyst in heterogeneous Pd-catalyzed coupling reactions, exhibits only 17% conversion after 30 min at r.t. [36,37]. In comparison, the greater catalytic activity of the Pd/G and Pd/GO over the commercial Pd/C catalyst may be attributed in part to the high level of purity of the starting graphite oxide support. In addition, TEM images of the commercially available Pd/C sample exhibit uneven size distributions of Pd nanoparticles within the catalyst with significant amounts of Pd agglomeration on the surface of the carbon support as (not shown). At lower catalyst loading of 0.1 mol %, Pd/G yields the product with 100% conversion after 2.5 h, in comparison with 95% with Pd/GO. Similarly, when 0.02 mol % loading was used, both catalysts still worked effectively, giving a conversion of 97% for Pd/G and 92% for Pd/GO after 4 h. However, further reducing the concentrations provided some insight into the relative reactivity of these two catalysts. With the lowest loading of 0.007 mol %, the reaction was completed after 5 h with Pd/G at r.t. affording a yield of 94% of product, whereas the Pd/GO displayed only 72% conversion under these conditions. Interestingly, at this low concentration, Pd/G is capable of converting 63% of the bromobenzene to the biphenyl product at 80° C. under microwave heating for 5 min. Following this reaction under the same conditions (80° C., MWI) led to 95% formation of product after 10 min. These results demonstrate the remarkable catalytic activity of Pd/G with a turnover number (TON) of 9000 and turnover frequency (TOF) of 108,000 (0.007 mol % Pd/G, 63% conversion at 80° C. under microwave heating for 5 min). To our knowledge, this is one of the highest turnover frequency (TOF) observed in a microwave-assisted Suzuki crosscoupling reaction by a Pd nanoparticles catalyst.

3.2.2. Recycling the Pd/G and Pd/GO Catalysts

Figure 13A:
FIGS. 13A and B. TEM images of (a) Pd/G after the 10th run and (b) Pd/GO after the 7th run.
Figure 13B:
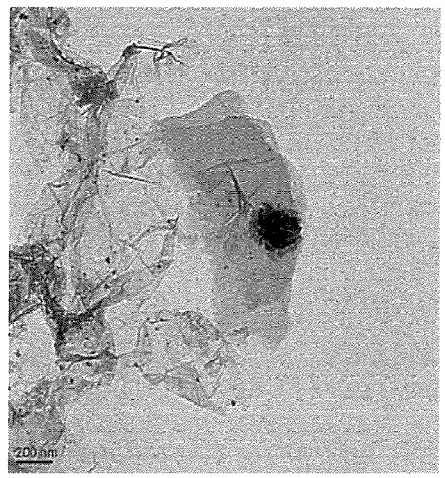

A significant practical application of heterogeneous catalysis is in the ability to easily remove the catalyst from the reaction mixture and reuse it for subsequent reactions until the catalyst is sufficiently deactivated. Thus, the ability to recycle the Pd/G and Pd/GO catalysts was studied for the Suzuki cross-coupling reaction of aryl bromide with phenyl boronic acid (Scheme 1) utilizing 0.3 mol % of these catalysts at 80° C. for 5 min using microwave irradiation as the heating source. After each reaction, the catalyst was recovered by simple washing with EtOH followed by decantation and re-used in a subsequent run. As shown in Table 1, the Pd/G nanoparticles can be easily recycled for eight times achieving a quantitative yield of the product. The activity of the catalyst dropped in runs 9 and 10, showing only 62% and 28% conversions, respectively. Evidence for deactivation of the Pd/G catalyst can be obtained from the TEM image (FIG. 13A) after the 10th run, which clearly demonstrates the agglomeration and accumulation of the Pd nanoparticles on the surface of graphene. This result indicates that the mechanism of deactivation of the catalyst is likely to involve the formation of aggregated Pd nanoparticles which leads to the decrease in the surface area and saturation of the coordination sites. After completion of the recycling experiments, the Pd/G was separated from the reaction mixture. The reaction solution was analyzed by ICP-MS, and the palladium content in the solution was determined to be 300 ppb. Such a small amount of leached palladium may argue against complete heterogeneity of the catalytic system in this reaction. However, further evidence on the nature of the catalytic mechanism is the failure to observe reactivity after the removal of the supported nanoparticles from the reaction medium. Thus, these results provide consistent implication for the proposed release and re-deposition mechanism [60-63] by which a small quantity of Pd leaches into the reaction solution catalyzes the reaction [62,63] and re-deposits to the surface of the graphene support at the end of the reaction. In this case, the large surface area created by the support can effectively facilitate both the Pd leaching into the solution to catalyze the reaction and the re-deposition of the leached Pd on the surface of the support after the reaction is completed. Similarly, the recyclability of Pd/GO was also examined using the same microwave-assisted Suzuki cross-coupling reaction conditions at 80° C. for 5 min (Table 1). In this case, full conversions were obtained in the runs 1-4. The activity slightly dropped in the fifth run yielding 96% conversion. The catalytic activity was further dropped in runs 6 and 7 to 54% and 23% conversions, respectively. Significant amounts of agglomeration of Pd nanoparticles on graphite oxide sheets can be observed on the TEM image prepared after the 7th run (FIG. 13B), indicating the possible deactivation pathway. Analysis of the reaction mixture by ICP-MS after the 7th run also displayed a very low palladium leaching of 350 ppb.

TABLE 1

Recycling experiments with Pd/G and Pd/GO catalysts using a concentration of 0.3 mol %.[a]

| Run | Conversion (%)[b] Pd/G | Conversion (%)[b] Pd/GO |
|---|---|---|
| 1 | 100 | 100 |
| 2 | 100 | 100 |
| 3 | 100 | 100 |
| 4 | 100 | 100 |
| 5 | 100 | 96 |
| 6 | 98 | 54 |
| 7 | 98 | 23 |
| 8 | 96 | 5 |
| 9 | 62 | — |
| 10 | 28 | — |
| 11 | 8 | — |

[a]Bromobenzene (50 mg, 0.32 mmol), boronic acid (47 mg, 0.382 mmol, 1.2 eq.), potassium carbonate (133 mg, 0.96 mmol, 3 eq.), and Pd/G (1.3 mg, 0.96 lmol, 0.3 mol %) in 4 mL (H$_2$O:EtOH) (1:1) were heated at 80° C. (MWI) for 5 min.
[b]Conversions were determined by GC-MS.

3.2.3. Activity of Pd/G Catalyst for the Preparation of Other Biphenyl Products To generalize the above results, the range of catalytic utility in Suzuki cross-coupling reactions for the preparation of other biphenyl products containing a broader range of functionality was investigated. For these experiments, we chose to use the Pd/G catalyst exclusively due to the superior catalytic activity demonstrated in the prior studies. As illustrated in FIG. 15, the Suzuki coupling of variously substituted aryl bromide and phenyl boronic acid reagents was carried out in the presence of 0.3 mol % Pd/G and potassium carbonate (3 eq.) using H$_2$O:EtOH (1:1) as environmentally benign solvents. The reactions are either completed at room temperature or heated under microwave irradiation (MWI) at 80° C. for 10 min. In this context, a broad range of aryl bromide containing electron-donating (1d-e) and electron-withdrawing groups (1a-c) can be effectively incorporated in the coupling products. In addition, phenyl boronic acids bearing useful functionality such as 4-dimethylamino (1c, g), 4-amino carbonyl (1d, f), or 4-thiomethyl (1b) all led to high yield of Suzuki products. We were pleased to find that even a more difficult substrate such as 4-nitro-1-chlorobenzene was able to undergo Suzuki coupling with phenyl boronic acid in good yield (1h).

3.3. Activity of Pd/G Catalyst Toward the Heck Reaction

Figure 16:
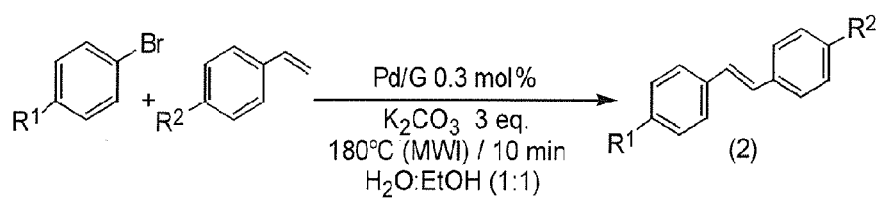
FIG. 16. Evaluation of catalysts for Heck reactions. a=Aryl bromide (0.51 mmol), alkene (1.02 mmol, 2 eq.), potassium carbonate (212 mg, 1.53 mmol, 3 eq.), Pd/G (2.1 mg, 1.53 mmol, 0.3 mol %) in 8 mL ($H_2O$:EtOH) (1:1) were heated at 180° C. (MWI) for 10 min.; b=Isolated yields.

To generalize the application of the Pd/G catalyst to another carbon-carbon bond forming process, the evaluation of the catalytic activity of the Pd/G catalyst was extended to the Heck reaction. While Heck reactions typically involve the use of phosphine-based palladium catalysis in homogeneous systems, we chose to examine our heterogeneous Pd/G nanoparticles under ligand-free conditions using microwave irradiation. Thus, the reaction of a diverse range of aryl bromides with a variety of olefins was evaluated using 0.3 mol % of Pd/G, potassium carbonate (3 eq.) and H$_2$O:EtOH as solvents at the temperature of 180° C. using a microwave irradiation as a heating source. As shown in FIG. 16, a variety of electron-rich (2d, g) and electron-poor (2c, f) aryl bromide substrates can easily undergo the Heck coupling with a relatively unactivated alkene such as tert-butylstyrene (2b, f), achieving an excellent yield of the Heck products.

3.4. Composition of Active Catalytic Species

Figure 5:
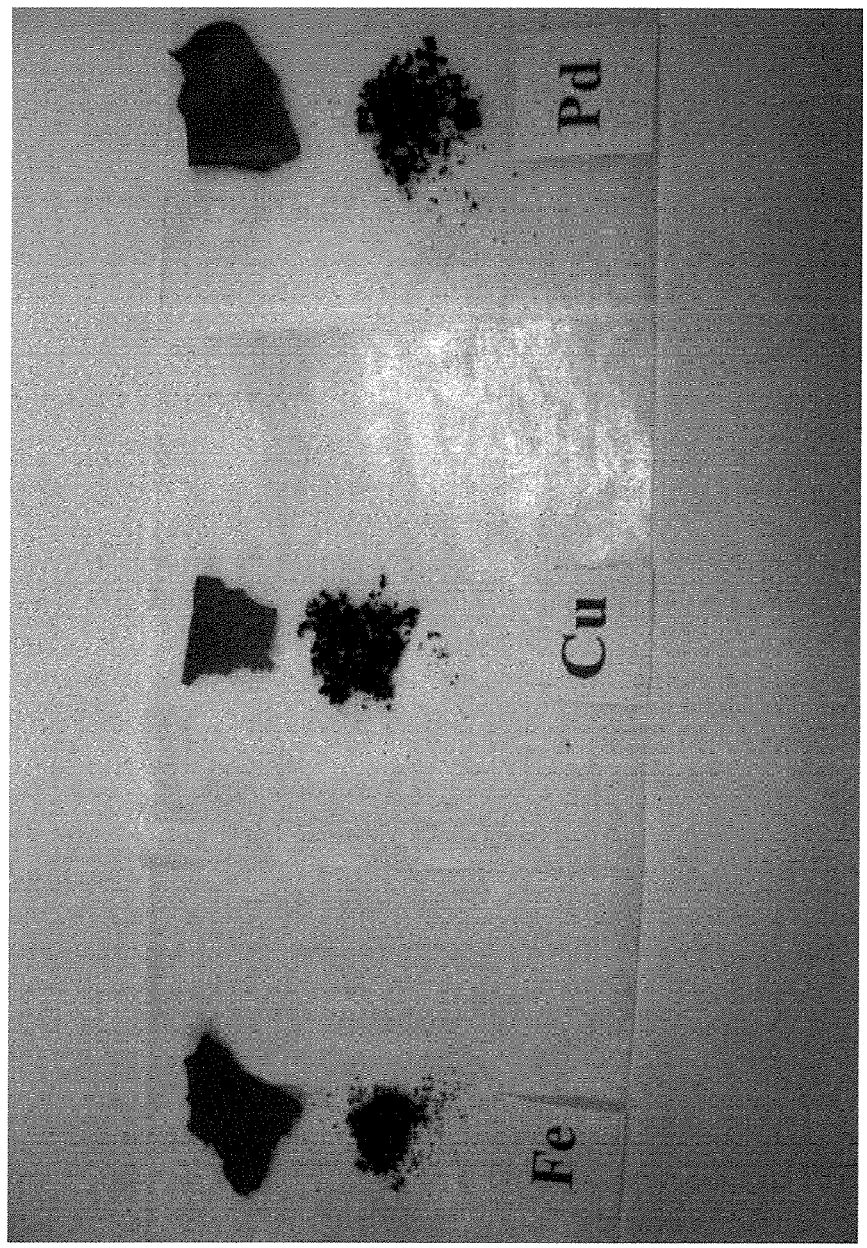
FIG. 5. Photographs of solid graphite oxide containing metal salts before (top) and after (bottom) microwave irradiation (MWI) of the solid.

The difference in the activity of the Pd/G and Pd/GO catalysts could be attributed to a number of parameters such as the nature and concentration of the active species, particle size, dispersion, and surface area. To gain further insight into the nature of the Pd species on the surface of graphene or GO support, we measured the XPS spectra of the Pd/G and Pd/GO catalysts before and after the Suzuki reaction in FIG. 5B at room temperature. The results shown in FIG. 14 indicate the presence of different oxidation states of Pd within the supported catalysts before and after the reaction.

The as-prepared Pd/GO catalyst consists mainly of Pd oxides as evident from the measured binding energies of the Pd $3d^{5/2}$ and $3d^{3/2}$ electrons at 337.8 and 343.2 eV, respectively corresponding to Pd(II). However, during the cross-coupling reaction, in situ reduction to Pd(0) occurs most likely by the solvent under basic conditions. The in situ reduction of Pd(II) is confirmed by the measured binding energies of the Pd $3d^{5/2}$ and $3d^{3/2}$ electrons after the reaction at 335.7 and 341 eV, respectively, thus corresponding to a mixture of Pd oxides and Pd(0) species. On the other hand, for the as-prepared Pd/G catalyst, part of the Pd(II) is already reduced to Pd(0) during the preparation of the catalyst by the HH reduction of the GO—Pd nitrate mixture under MWI. This is clearly illustrated in FIG. 14 by the almost identical XPS spectra of the Pd/GO catalyst after the reaction and the Pd/G catalyst before the reaction. Following the cross-coupling reaction, in situ reduction of the remaining Pd(II) species in the Pd/G catalyst converts the catalyst to mostly Pd(0) species, which are the active species in Pd-catalyzed cross-coupling reactions.

The remarkable activity and recyclability of the Pd/G catalyst appears to be clearly related to the high concentration of Pd(0) species already present in the as-prepared catalyst in contrast to the Pd/GO in which palladium reduction occurs in situ during the reaction. Tyhus, a systematic examination of the effect of increasing the concentration of the Pd(0) in the Pd/G catalyst on the catalytic activity is carried out. For this purpose, the catalytic activities of different Pd/G catalysts with similar particle size but different concentrations of Pd(0) are compared.

Figure 14:
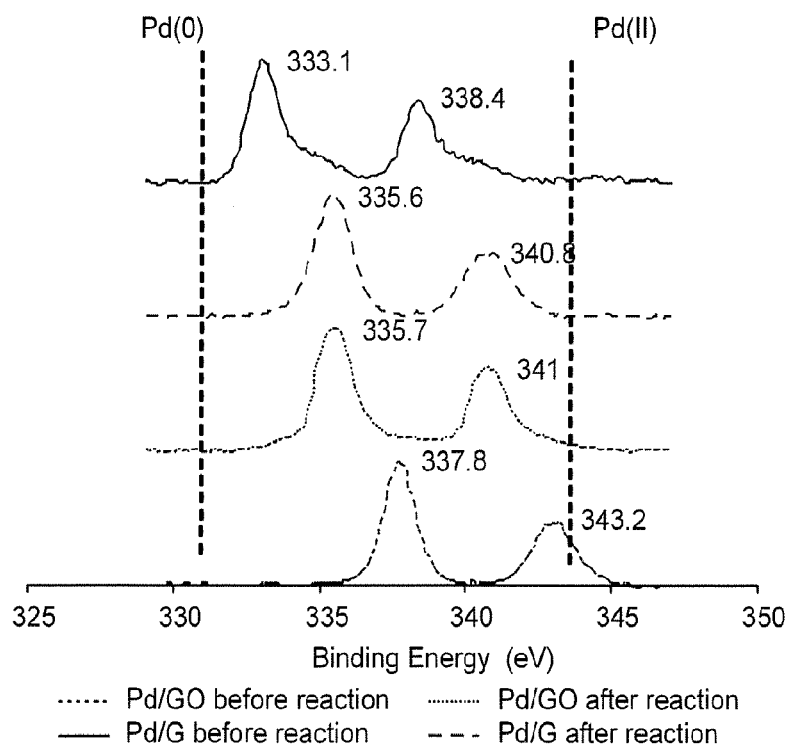
FIG. 14. XPS spectra of the Pd 3d5/2 and 3d3/2 electrons' binding energies for Pd/G and Pd/GO catalysts before and after Suzuki reactions.

We attribute the great reactivity of the Pd/G catalysts prepared by MWI to the small size of the Pd nanoparticles (7-9 nm), the high degree of dispersion due to the lack of evidence for agglomeration of the nanoparticles during the preparation, and the high concentration of the Pd(0) species already present in the as-prepared catalyst (XPS results, FIG. 14). It is noteworthy that the palladium nitrate source used for catalyst preparation has excellent solubility in water, and there is no concern regarding the possibility of precipitating the palladium nitrate on GO. Furthermore, the current MWI procedure is a very effective technique for simultaneous reduction of both the Pd ions (from palladium nitrate) and GO using HH, providing a rapid temperature rise during microwave heating in water, thus leading to a fast nucleation and consequently small uniform Pd nanoparticles (7-9 nm) well dispersed on the resulting graphene sheets (TEM results, FIG. 10A). It should be noted that the simultaneous reduction of GO and the Pd ions in solution followed by the heterogeneous nucleation of Pd nanoparticles on the large surface area of graphene is the most important and unique feature of our MWI synthesis approach of the highly active Pd/G catalyst. We have previously demonstrated that simple physical mixing of separately prepared very small Pd nanoparticles (4-6 nm) and reduced GO sheets results in significant aggregation of the Pd nanoparticles with very poor dispersion on the graphene sheets [28]. On the other hand, the simultaneous reduction of the Pd ions with GO results in well-dispersed nanoparticles on the graphene sheets, thus suggesting that specific interaction between the Pd nanocrystals and the graphene sheets may be responsible for dispersion of the nanoparticles. This is also consistent with the enhanced thermal stability of the Pd/G over the graphene sheets as shown in FIG. 11A. Furthermore, our results indicate that the simultaneous reduction of GO and the Pd ions results in a higher concentration of the catalytically active Pd(0) in the as-prepared catalyst which enhances the nearly dominant heterogeneous nature of the catalytic reaction system. Therefore, the current work clearly demonstrates that the catalyst preparation method exerts the major influence in determining the properties and hence the activity of the catalyst. In addition, the significance of graphene as an ideal support system for palladium can also be attributed to its remarkable structural and electronic features. The unique hexagonal planar structure of the graphene and the presence of C=C bonds within the graphene matrix may play an important role as an electron-rich labile support system for palladium, which stabilizes the metal center, prevents deactivation of the catalyst by agglomeration, and increases the catalytic activity of the palladium nanoparticles for cross-coupling reactions.

4. CONCLUSIONS

In conclusion, we have developed an efficient method to generate highly active Pd nanoparticles supported on graphene by microwave-assisted chemical reduction of the corresponding aqueous mixture of palladium nitrate and dispersed graphite oxide sheets. These catalysts offer a number of advantages such as high stability of the catalyst, easy removal from the reaction mixture, reusability of the catalyst for eight times with minimal loss of activity, and significantly better performance than the well-known commercial Pd/C catalyst. Both Pd/G and Pd/GO demonstrated excellent catalytic activity for the carbon-carbon cross-coupling reactions under ligand-free ambient conditions in an environmentally friendly solvent system. However, the Pd/G containing 7.9 wt. % palladium demonstrated a remarkable turnover frequency ($108,000$ $h^{-1}$) in the Suzuki cross-coupling reactions using MWI heating conditions. We also found strong evidence that the outstanding reactivity and recyclability of the Pd/G catalyst toward Suzuki cross-coupling reactions is associated with high concentration of Pd(0) nanoparticles very well dispersed on the surface of the graphene sheets. This catalyst also demonstrated a broad range of utility for Heck coupling reactions.

REFERENCES FOR EXAMPLE 1

[1] A. K. Geim, Science 324 (2009) 1530.
[2] A. K. Geim, Nat. Mater. 6 (2007) 183.
[3] K. S, Novoselov, A. K. Geim, S. V. Morozov, D. Jiang, M. L. Katsnelson, I. V. Grigorieva, S. V. Dubonos, A. A. Firsov, Nature 438 (2005) 197.
[4] K. S, Novoselov, A. K Geim, S. V. Morozov, D. Jiang, Y. Zhang, S. V. Dubonos, I. V. Grigorieva, A. A. Firsov, Science 306 (2004) 666.
[5] M. J. Allen, V. C. Tung, R. B. Kaner, Chem. Rev. 110 (2009) 132.
[6] C. N. R. Rao, A. K. Sood, K. S. Subrahmanyam, A. Govindaraj, Angew. Chem. Int. Ed. 48 (2009) 7752.
[7] J. Wu, W. Pisula, K. Müllen, Chem. Rev. 107 (2007) 718.
[8] S. Stankovich, D. A. Dikin, G. H. B. Dommett, K. M. Kohlhaas, E. J. Zimney, E. A. Stach, R. D. Piner, S. T. Nguyen, R. S. Ruoff, Nature 442 (2006) 282.
[9] S. Watcharotone, D. A. Dikin, S. Stankovich, R. Piner, I. Jung, G. H. B. Dommett, G. Evmenenko, S. E. Wu, S. F. Chen, C. P. Liu, S. T. Nguyen, R. S. Ruoff, Nano Lett. 7 (2007) 1888.
[10] G. Eda, G. Fanchini, M. Chhowalla, Nat. Nanotechnol. 3 (2008) 270.
[11] V. C. Tung, M. J. Allen, Y. Yang, R. B. Kaner, Nat. Nanotechnol. 4 (2009) 25.
[12] P. V. J. Kamat, Phys. Chem. Lett. 1 (2010) 520.
[13] B. Seger, P. V. Kamat, J. Phys. Chem. C 113 (2009) 7990.
[14] G. Williams, B. Seger, P. V. Kamat, ACS Nano 2 (2008) 1487.
[15] Y. C. Si, E. T. Samulski, Chem. Mater. 20 (2008) 6792.
[16] C. Xu, X. Wang, J. W. Zhu, J. Phys. Chem. C 112 (2008) 19841.
[17] R. Muszynski, B. Seger, P. V. Kamat, J. Phys. Chem. C 112 (2008) 5263.
[18] G. Goncalves, P. A. A. P. Marques, C. M. Granadeiro, H. I. S, Nogueira, M. K. Singh, J. Gracio, Chem. Mater. 21 (2009) 4796.
[19] X. Zhou, X. Huang, X. Qi, S. Wu, C. Xue, F. Y. C. Boey, Q. Yan, P. Chen, H. Zhang, J. Phys. Chem. C 113 (2009) 10842.
[20] Y. H. Lu, M. Zhou, C. Zhang, Y. P. Feng, J. Phys. Chem. C 113 (2009) 20156.
[21] K. S, Novoselov, Z. Jiang, Y. Zhang, S. V. Morozov, H. L. Stormer, U. Zeitler, J. C. Maan, G. S. Boebinger, P. Kim, A. K. Geim, Science 315 (2007) 1379.

[22] C. Gomez-Navarro, M. Burghard, K. Kern, Nano Lett. 8 (2008) 2045.
[23] Z. Luo, L. A. Somers, Y. Dan, T. Ly, N. J. Kybert, E. J. Mele, A. T. Charlie Johnson, Nano Lett. 10 (2010) 777.
[24] S. Park, R. S. Ruoff, Nat. Nanotechnol. 4 (2009) 217.
[25] S. Stankovich, R. D. Piner, X. Chen, N. Wu, S. T. Nguyen, R. S. Ruoff, J. Mater. Chem. 16 (2006) 155.
[26] S. Stankovich, D. A. Dikin, R. D. Piner, K. M. Kohlhaas, A. Kleinhammes, Y. Jia, Y. Wu, S. T. Nguyen, R. S. Ruoff, Carbon 45 (2007) 1558.
[27] S. Park, J. An, I. Jung, R. D. Piney, S. J. An, X. Li, A. Velamakanni, R. S. Ruoff, Nano Lett. 9 (2009) 1593.
[28] H. M. A. Hassan, V. Abdelsayed, A. E. R. Khder, K. M. AbouZeid, J. Terrier, M. S. El-Shall, S. I. Al-Resayes, A. El-Azhary, J. Mater. Chem. 19 (2009) 3832.
[29] S. L. Buchwald, Acc. Chem. Res. 41 (2008) 1439.
[30] L. Yin, J. Liebscher, Chem. Rev. 107 (2007) 133.
[31] R. F. Heck, Acc. Chem. Res. 12 (1979) 146.
[32] N. Miyaura, A. Suzuki, Chem. Rev. 95 (1995) 2457.
[33] I. P. Beletskaya, A. V. Cheprakov, Chem. Rev. 100 (2000) 3009.
[34] C. J. Welch, J. Albaneze-Walker, W. R. Leonard, M. Biba, J. DaSilva, D. Henderson, B. B. Laing, D. J. Mathre, S. Spencer, X. Bu, T. Wang, Org. Process Res. Dev. 9 (2005) 198.
[35] C. E. Garrett, K. Prasad, Adv. Synth. Catal. 346 (2004) 889.
[36] B. M. Bhanage, M. Arai, Catal. Rev. 43 (2001) 315.
[37] K. Köhler, R. G. Heidenreich, S. S. Soomro, S. S. Pröckl, Adv. Synth. Catal. 350 (2008) 2930.
[38] L. Djakovitch, K. Koehler, J. Am. Chem. Soc. 123 (2001) 5990.
[39] L. Djakovitch, K. Koehler, J. Mol. Catal. A: Chem. 142 (1999) 275.
[40] J. Li, A. W. H. Mau, C. R. Strauss, Chem. Commun. (1997) 1275.
[41] H. Erdogan, Ö. Metin, S. Özkar, Phys. Chem. Chem. Phys. 11 (2009) 10519.
[42] R. Narayanan, M. El-Sayed, J. Am. Chem. Soc. 125 (2003) 8340.
[43] R. Narayanan, M. El-Sayed, J. Phys. Chem. B 108 (2004) 8572.
[44] C. Duanmu, I. Saha, Y. Zheng, B. M. Goodson, Y. Gao, Chem. Mater. 18 (2006) 5973.
[45] R. Narayanan, M. Tabor, M. El-Sayed, Top. Catal. 48 (2008) 60.
[46] P. J. Ellis, I. J. S. Fairlamb, S. F. J. Hackett, K. Wilson, A. F. Lee, Angew. Chem. Int. Ed. 49 (2010) 1820.
[47] S. Wittmann, A. Schatz, R. N. Grass, W. J. Stark, O. Reiser, Angew. Chem. Int. Ed. 49 (2010) 1867.
[48] M. Irfan, M. Fuchs, T. N. Glasnov, C. O. Kappe, Chem. Eur. J. 15 (2009) 11608.
[49] G. M. Scheuermann, L. Rumi, P. Steurer, W. Bannwarth, R. Mülhaupt, J. Am. Chem. Soc. 131 (2009) 8262.
[50] J. A. Gerber, D. Magana, A. Washington, G. F. Strouse, J. Am. Chem. Soc. 127 (2005) 15791.
[51] A. B. Panda, G. P. Glaspell, M. S. El-Shall, J. Am. Chem. Soc. 128 (2006) 2790.
[52] A. B. Panda, G. P. Glaspell, M. S. El-Shall, J. Phys. Chem. C 111 (2007) 1861.
[53] V. Abdelsayed, A. B. Panda, G. P. Glaspell, M. S. El-Shall, in: R. Nagarajan, T. Alan Hatton, (Eds.), Nanoparticles: Synthesis, Stabilization, Passivation, and Functionalization, ACS Symposium Series, 2008, p. 996 (Chapter).
[54] V. Abdelsayed, A. Aljarash, M. S. El-Shall, Z. A. Al Othman, A. H. Alghamdi, Chem. Mater. 21 (2009) 2825.
[55] M. Larhed, C. Moberg, A. Hallberg, Acc. Chem. Res. 35 (2002) 717.
[56] W. S. Hummers Jr., R. E. Offeman, J. Am. Chem. Soc. 80 (1958) 1339.
[57] A. C. Ferrari, Solid State Commun. 446 (2007) 60.
[58] S. Berciaud, S. Ryu, L. E. Bras, T. F. Heinz, Nano Lett. 9 (2009) 346.
[59] M. S. Dresselhaus, A. Jorio, M. Hofmann, G. Dresselhaus, R. Saito, Nano Lett. 10 (2010) 751.
[60] I. W. Davies, L. Matty, D. L. Hughes, P. J. Reider, J. Am. Chem. Soc. 123 (2001) 10139.
[61] K. Köhler, R. G. Heidenreich, J. G. E. Krauter, J. Pietsch, Chem. Eur. J. 8 (2002) 622.
[62] N. E. Leadbeater, V. A. Williams, T. M. Barnard, M. J. Collins, It was demonstrated that ultra-low amounts of Pd loading can effectively catalyze the Suzuki and Heck coupling reactions, Org. Process Res. Dev. 10 (2006) 833.
[63] R. K. Arvela, N. E. Leadbeater, J. Org. Chem. 70 (2005) 1786.
[64] N. Herring, A. R. Siamaki, S. Moussa, F. Gupton, M. S. El-Shall, in preparation.

Example 3

Applications of Pd Supported on Graphene (Pd/G) for Sonogashira Reactions

The PdG catalysts of the invention were also used to carry out Sonogashira reactions using heterogeneous Pd on graphene (Pd/G) nanoparticles:

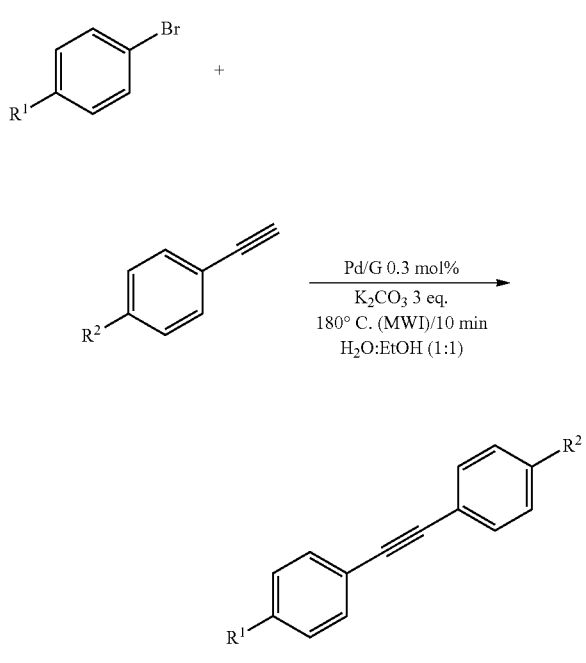

| Entry | Aryl-halide | Alkyne | Product (isolated %) |
|---|---|---|---|
| 1 | 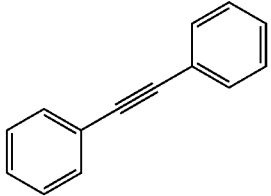 | | 98% |
| 2 | | | 92% |
| 3 | | | 95% |
| 4 | | | 88% |
| 5 | | | 90% |
| 6 | | | 91% |

Example 4

Methods for the Production of Graphene and Metal Nanoparticles Supported on Graphene Using Microwave Assisted Chemical Reduction in Solution A facile and scalable chemical reduction method assisted by microwave irradiation has been developed for the synthesis of chemically converted graphene sheets and metal nanoparticles supported on the large surface area of the thermally stable 2D graphene sheets.

We have developed a facile and scalable chemical reduction method assisted by microwave irradiation for the synthesis of chemically converted graphene sheets and metal nanoparticles dispersed on the graphene sheets. The method allows rapid chemical reduction of exfoliated graphite oxide (GO) using a variety of reducing agents in either aqueous or organic media. It also allows the simultaneous reduction of GO and a variety of metal salts thus resulting in the dispersion of metallic and bimetallic nanoparticles supported on the large surface area of the thermally stable 2D graphene sheets.

Graphene, a single hexagonally flat layer of graphite, has attracted great interest both for a fundamental understanding of its unique structural and electronic properties and for important potential applications in nanoelectronics and devices.[1-5] The unique properties of this two-dimensional (2D) material include the highest intrinsic carrier mobility at room temperature of all known materials and very high mechanical strength and thermal stability.[2,6-9] Graphene holds great promise for the development of new composite materials, emissive displays, ultrasensitive detectors and micromechanical resonators.[1-9] The combination of high mobility, thermal, chemical and mechanical stability with the high surface area offers many interesting applications in a wide range of fields including heterogeneous catalysis where metallic and bimetallic nanoparticle catalysts can be efficiently dispersed on the graphene sheets.[10-12] In many cases, the remarkable properties of single graphene layers extend to bilayers and a few layers of graphene sheets.[1,13-16]

Several methods have been reported for the production of graphene sheets including micromechanical cleavage and thermal expansion of graphite,[1,2,17,18] epitaxial growth on SiC surfaces[4,13] and chemical reduction of exfoliated graphite oxide (GO).[3,19-22] In most of the reported methods, high temperatures and long processing times are required. For example, the thermal exfoliation of GO requires heating to above 1000° C.[17,18] Microwave plasma enhanced chemical vapor deposition (MW-PECVD) requires substrates that withstand elevated temperatures up to 700° C. and results in the formation of 4-6 layers of stacked graphene sheets.[15] Recently, a substrate-free microwave plasma process has been demonstrated for the synthesis of graphene sheets but it requires a relatively complicated flow plasma reactor.[23] The chemical reduction methods of exfoliated GO with reducing agents such as hydrazine hydrate provide a promising approach for the efficient large scale production of chemically converted graphene (CCG) sheets.[19-22] However, in most cases heating to nearly 100° C. over several hours is required.[19-22] Herein, we describe a facile, convenient and scalable method for the synthesis of CCG sheets as well as metallic and bimetallic nanoparticles supported on the CCG sheets using a simple household microwave oven.

Microwave irradiation (MWI) has been demonstrated for the synthesis of a variety of nanomaterials including metals, metal oxides, bimetallic alloys and semiconductors with controlled size and shape without the need for high temperature or high pressure.[24-27] MWI has also been used for the synthesis of soluble single wall carbon nanotube derivatives[28] and for the exfoliation of graphite intercalation compounds.[29] The main advantage of MWI over other conventional heating methods is heating the reaction mixture uniformly and rapidly. Due to the difference in the solvent and reactant dielectric constants, selective dielectric heating can provide significant enhancement in the transfer of energy directly to the reactants which causes an instantaneous internal temperature rise. The method reported here allows the rapid chemical reduction of GO using a variety of reducing agents in either aqueous or organic media. It also allows the simultaneous reduction of GO and a variety of metal salts thus resulting in the synthesis of metallic and bimetallic nanoparticles supported on the CCG sheets.

Figure 17A:
FIGS. 17A and B (a) Images of the graphite oxide (GO) suspension in water before and after MWI in the presence of the reducing agents ethylenediamine (EDA), ammonium hydroxide (AH) and hydrazine hydrate (HD). (b) XRD patterns of graphite, GO, and graphene prepared by MWI of GO using hydrazine hydrate as a reducing agent.

In the experiments, GO was prepared by the oxidation of high purity graphite powder (99.9999%, 200 mesh, Alfa Aesar) with $H_2SO_4/KMnO_4$ according to the method of Hummers and Offeman.[30] After repeated washing of the resulting yellowish-brown cake with hot water, the powder was dried at room temperature under vacuum overnight. 0.1 g of the dried GO was sonicated in 20 ml of deionized water until a homogeneous yellow dispersion was obtained (see FIG. 17A). The GO can be dispersed easily in water due to the presence of a variety of hydrophilic oxygen groups (OH, O, COOH) on the basal planes and edges.[18,20-22] The solution was placed inside a conventional microwave after adding 100 ml of the reducing agent [hydrazine hydrate (HH) (Sigma Aldrich), ethylenediamine (EDA) (Sigma Aldrich) or ammonium hydroxide (AH) (Sigma Aldrich)]. The microwave oven (Emerson MW8119SB) was then operated at full power (1000 W), 2.45 GHz, in 30 s cycles (on for 10 s, off and stirring for 20 s) for a total reaction time of 60 s. The yellow dispersion of GO gradually changed to a black color indicating the completion of the chemical reduction to graphene. The graphene sheets were separated by using an Eppendorf 5804 centrifuge operated at 5000 rpm for 15 min and dried overnight under vacuum. For the preparation of the Pd, Cu and PdCu nanoparticles supported on the graphene sheets, an appropriate amount of Pd nitrate (10 wt. % in 10 wt. % $HNO_3$, 99.999%, Sigma Aldrich), Cu nitrate (ACS reagent, 98%, Sigma Aldrich) or a mixture of both was added to the GO solution in water containing the reducing agent before the MWI. For example, in a typical experiment, a mixture of 50 mg GO in 25 ml deionized water, 100 µl HH and 100 µl Pd nitrate was MW irradiated for 20-30 s.

The same method was also used for the preparation of organically passivated Au, Ag and Cu nanoparticles supported on the CCG sheets. In this case, GO was dispersed in oleylamine (70%, Sigma Aldrich) or in a 1:1 (mol ratio) mixture of oleylamine and oleic acid (90%, Sigma Aldrich), then an appropriate amount of $HAuCl_4$ (99.99%, 30 wt. % in dilute HCl, Sigma Aldrich), or Ag acetate (99.99%, Sigma Aldrich) or Cu acetate (99.99%, Sigma Aldrich) was added while stirring. The mixture was then placed in the microwave oven for reaction times that varied from 1-2 min. The resulting mixture was diluted with toluene and centrifuged for 5 min to remove the free nanoparticles from the supported ones on the CCG sheets. The sample was then dried under vacuum overnight. The dried sample was dispersed in toluene using a sonicator bath and the resulting solution was used for the UV-Vis absorption and the transmission electron microscopy (TEM) measurements. The optical absorption spectra were measured using a HP-8453 spectrophotometer and the TEM images were obtained using a Joel JEM-1230 electron microscope operated at 120 kV equipped with a Gatan UltraScan 4000SP 4K×4K CCD camera. Samples for TEM were prepared by placing a droplet of a colloid suspension in toluene on a Formvar carbon-coated, 300-mesh copper grid (Ted Pella) and allowed to evaporate in air at room temperature. The small angle X-ray diffraction (SA-XRD) patterns were measured at room temperature with an X'Pert Philips Materials Research Diffractometer using CuKa radiation. Scanning electron microscopy (SEM) and energy dispersive X-ray spectroscopy (EDS) was carried out using a Quantum DS-130S Dual Stage Electron Microscope. The morphology of the CCG sheets was examined by an atomic force microscope (Nano-Scope Ma, Digital Instruments) using tapping mode. The thermal gravimetric analysis was done on a TGA Q5000 from TA instruments. The Raman spectra were measured using an excitation wavelength of 457.9 nm provided by a Spectra-Physics model 2025 argon ion laser. The laser beam was focused to a 0.10 mm diameter spot on the sample with a laser power of 1 mW. The samples were pressed into a depression at the end of a 3 mm diameter stainless steel rod, held at a 30 degree angle in the path of the laser beam. The detector was a Princeton Instruments 1340×400 liquid nitrogen CCD detector, attached to a Spex model 1870 0.5 meter single spectrograph with interchangeable 1200 and 600 lines/mm holographic gratings (Jobin-Yvon). The Raman scattered light was collected by a Canon 50 mm f/0.95 camera lens. Though the holographic gratings provided high discrimination, Schott and Corning glass cut-off filters were used to provide additional filtering of reflected laser light, when necessary.

Figure 17B:
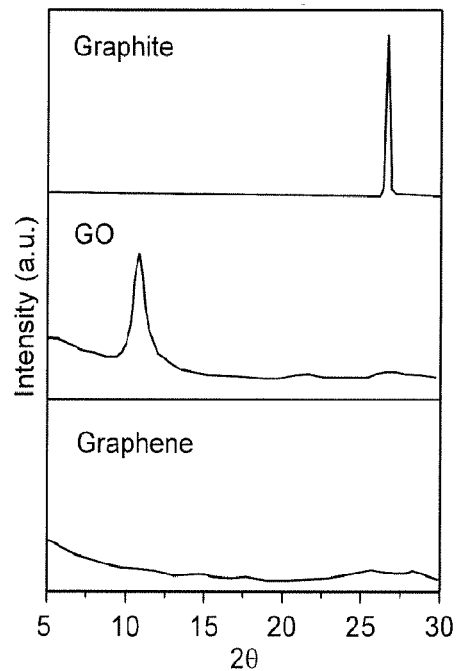

FIG. 17A displays a digital photograph of the exfoliated GO dispersed in water (5 mg/mL) before and after MWI in the presence of the reducing agents ethylenediamine (EDA), ammonium hydroxide (AH) and hydrazine hydrate (HH). Following MWI for 30-60 s in the presence of the reducing agent, the yellow-brown color of the dispersed GO in water changed to black indicating the reduction of the GO. This reduction is supposed to lead to deoxygenation of the GO (removal of oxygen functionalities such as hydroxyl and epoxide groups) and to significant restoration of the $sp^2$ carbon sites and re-establishment of the conjugated graphene network.[19,20] It has been shown that HH is one of the best reducing agents for the chemical reduction of exfoliated GO to produce very thin graphene sheets, although the chemical pathways for the GO reduction remain unclear.[19-22] In addition to HH, we found that MWI of exfoliated GO in the presence of EDA and AH could also lead to fast deoxygenation, consistent with a recent report where graphene suspensions were prepared by heating exfoliated GO in NaOH or KOH at moderate temperatures (50-90° C.).[22] Detailed characterizations of the CCG sheets produced by the MWI in the presence of the three reducing agents EDA, AH and HH are currently under way to understand the role of each reducing agent in the deoxygenation of GO. The results reported in this communication are focused only on the HH reduction under MWI. The XRD patterns displayed in FIG. 17B confirm the chemical reduction of the GO and the formation of CCG sheets using HH as the reducing agent.[21,22] The initial graphite powder shows the typical sharp diffraction peak at 2θ=26.658o with the corresponding d-spacing of 3.34 Angstroms. The oxidation process results in the insertion of hydroxyl and epoxy groups between the carbon sheets mainly on the centers while the carboxyl groups are typically inserted on the terminal and lateral sides of the sheets.[18] The insertion of these groups leads to decreasing the van der Waals forces between the graphite sheets in the exfoliated GO. As shown in FIG. 17B, the XRD pattern of the exfoliated GO shows no diffraction peaks from the parent graphite material but a new broad peak at 2θ=10.89° with a d-spacing of 8.14 Angstroms is observed. This indicates that the distance between the carbon sheets has increased due to the insertion of interplanar groups. The GO sheets are expected to be thicker than the graphite sheets due to the presence of covalently bounded oxygen atoms and the displacement of the sp3-hybridized carbon atoms slightly above and below the original graphene sheets. After MWI of the GO in the presence of HH as the reducing agent, the XRD pattern of the resulting CCG sheets shows the disappearance of the 10.89° peak confirming the complete reduction of the GO sheets.18

Figure 18A:
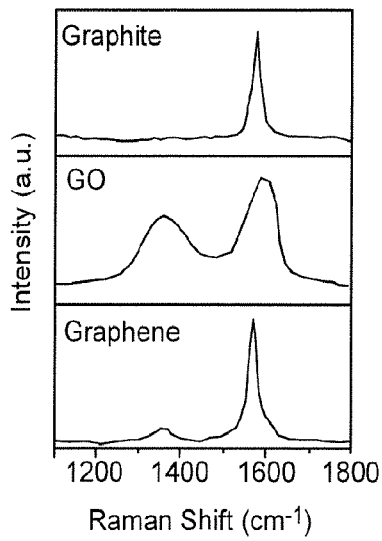
FIGS. 18A and B A, Raman spectra of the original graphite sample, the exfoliated graphite oxide (GO) and the chemically converted graphene using MWI of GO in the presence of HH. B, Raman spectrum of the chemically converted graphene in the region of the 2D band showing a strong broad peak around 2700 $cm^{-1}$.
Figure 18B:
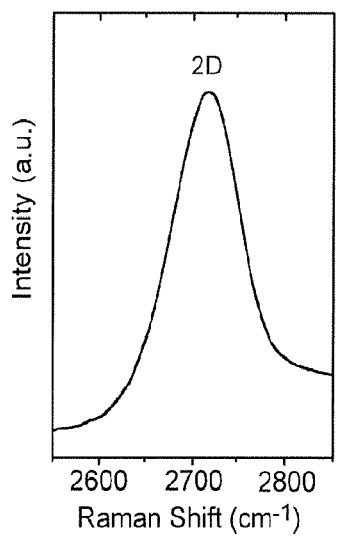

Raman spectroscopy is one of the most widely used techniques to characterize the structural and electronic properties of graphene including disorder and defect structures, defect density and doping levels.[31,32] The Raman spectrum of graphene is characterized by three main features, the G mode arising from emission of zone-center optical phonons (usually observed at ~1575 $cm^{-1}$), the D mode arising from the doubly resonant disorder-induced mode (~1350 $cm^{-1}$) and the symmetry-allowed 2D overtone mode (~2700 $cm^{-1}$)[31,32] The shift and line shape associated with these modes have been used to distinguish single, free-standing graphene sheets from bilayer and few-layer graphene (FLG).[31,32] To characterize the properties of the CCG, we measured the Raman spectra of the original graphite, GO and the as-prepared CCG sheets (by MWI in the presence of HH) using 457.9 nm radiation from an Ar-ion laser. The results are shown in FIG. 18. Raman spectrum of the graphite powder shows the in-phase vibration of the graphite lattice at 1575 $cm^{-1}$ (G band). The spectrum of the exfoliated GO shows a broadened and blue shifted G-band (1594 $cm^{-1}$) and the D-band with low intensity at 1354 $cm^{-1}$. The blue shift of the G band in GO is usually attributed to the presence of isolated double bonds which resonate at higher frequencies than the G band of graphite.[33] The spectrum of the CCG shows a strong G-band around 1571 $cm^{-1}$ almost at the same frequency as that of graphite with a small shoulder, identified as the D0-band around 1616 $cm^{-1}$, and a weak D-band around 1357 $cm^{-1}$. The D-band at 1357 $cm^{-1}$ and the D0-shoulder at 1616 $cm^{-1}$ have been attributed to structural disorder at defect sites and finite size effects, respectively.[15,23,31,34] The intensity ratio of the D-band to the G-band is used as a measure of quality of the graphitic structures since for highly ordered pyrolytic graphite this ratio approaches zero.[15,35] As shown in FIG. 18, the Raman spectrum of the CCG sheets exhibits a weak disorder-induced D band with the D to G intensity ratio of only 0.10-0.12 thus indicating the high quality of the synthesized graphene sheets. It is also interesting to note that the frequency of the G-mode in the synthesized CCG sheets (1571 $cm^{-1}$) is very similar to that observed in the graphite powder (1575 $cm^{-1}$) and significantly different from that of the GO (1594 $cm^{-1}$). The same trend has been found in the frequency of the G-mode of the freestanding graphene layer which is appreciably downshifted as compared with that of the supported layer.[32] The overall features of the G-band observed in our CCG sheets are consistent with the Raman spectra reported for FLG.[15,23,31,36] We have also observed the high energy second-order 2D-band of the synthesized graphene sheets around 2700 $cm^{-1}$, as shown in FIG. 18B. The position and shape of the 2D peak depend on the number of graphene layers, and therefore the 2D peak can be used to distinguish between single-layer, bilayer, and FLG.[23,31] For example, it has been shown that a single-layer graphene exhibits a single, sharp 2D band located below 2700 $cm^{-1}$ while bilayer sheets have a broader 2D peak at ~2700 $cm^{-1}$.[31] Sheets with more than five layers have broad 2D peaks significantly shifted to positions greater than 2700 $cm^{-1}$.[31] Since our synthesized graphene sample shows a single 2D band around 2720 $cm^{-1}$, it can be concluded that the analyzed region of the sample consisted of FLG probably with five or more layers.

Figure 19A:
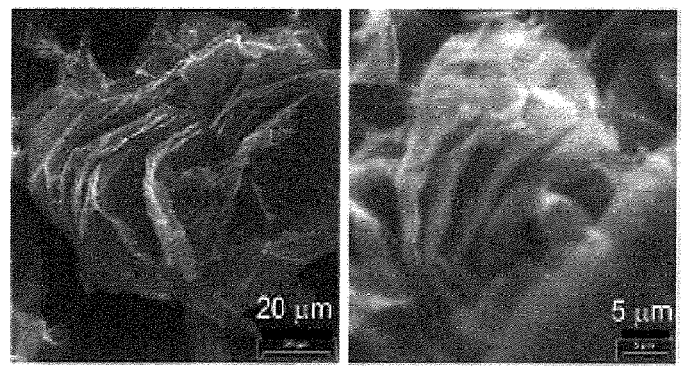
FIGS. 19A and B. (a) SEM and (b) TEM images of the chemically converted graphene sheets using MWI of GO in the presence of HH.
Figure 19B:
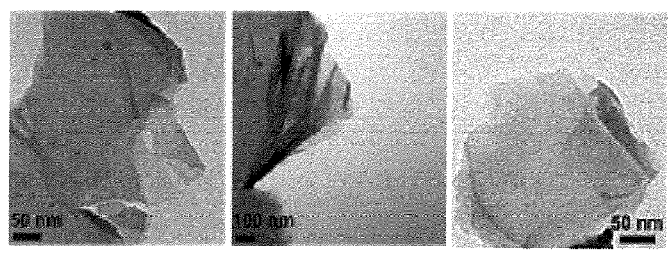

FIG. 19 displays typical SEM and TEM images of the synthesized graphene sheets by MWI in the presence of HH. The SEM micrographs clearly show extended sheets of lateral dimensions ranging from a few micrometers to tens of micrometers in length with layered structures. The TEM images show a few stacked layers (2-3 layers) and a lateral size up to a few micrometers. Also the TEM images show that some of the graphene layers are folded on one edge with isolated small fragments on the surfaces.

Figure 20A:
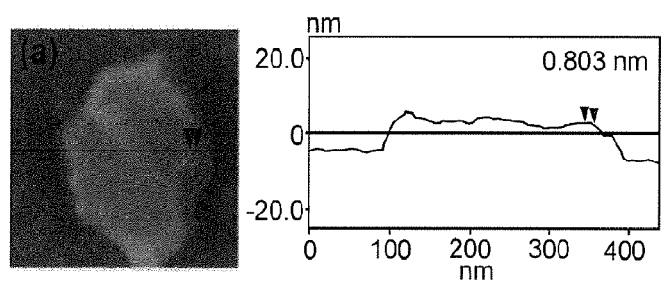
FIG. 20A-C. AFM images and cross-section analysis of the as-prepared chemically converted graphene sheets (using MWI of GO in the presence of HH) deposited from a suspension on a freshly cleaved mica substrate. No ultrasonic treatment was done on the suspension. A-C show different thickness of graphene sheets.
Figure 20B:
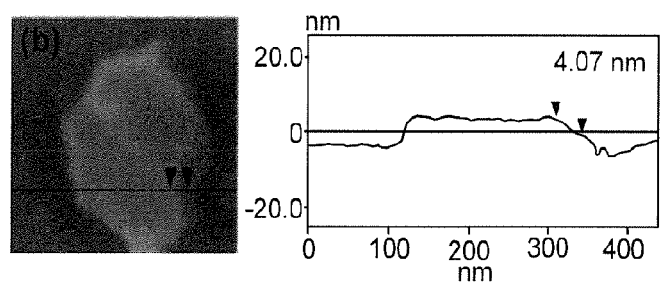
Figure 20C:
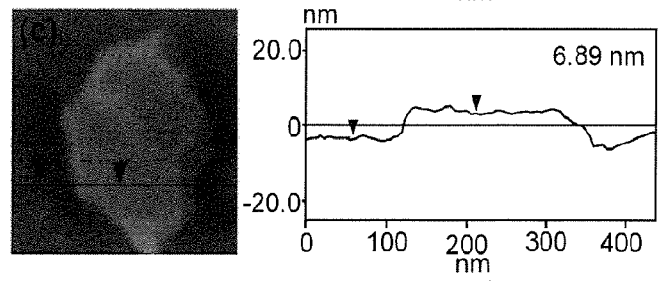

AFM images were obtained to measure the thickness of the FLG, and representative images are shown in FIG. 20. The as-prepared graphene sample, using MWI in the presence of HH, was dispersed in ethanol and a droplet of the suspension was placed on a freshly cleaved mica surface. No ultrasonic treatment was done in order to determine the thickness of the as-prepared graphene flakes. The AFM images show that the FLG flakes have lateral dimensions of several hundreds of nanometers. The cross-section analysis shows that the FLG sheets are stacked together within the flake in terrace morphology as shown in FIG. 20. The distance between the closest graphene sheets was determined to be 0.803 nm (FIG. 20A). This is consistent with the reported AFM results on FLG sheets, where the single layer graphene is ~1 nm.[1,17,20,21] The AFM images of several FLG flakes clearly display a variation of thickness across the flake. This is due to the terrace stacking and also the folding and wrapping of the sheets. For example, the measured heights between the arrows in the cross-section analysis shown in FIGS. 20 B and C were found to be 4.07 and 6.89 nm thus corresponding to about 5 and 8 graphene layers, respectively. The smallest and largest thicknesses found across the flakes were ~1 nm and 6.89 nm, respectively. This indicates that the as-prepared FLG flakes contain between 1-8 sheets. By using multiple ultrasonic treatments of the as-prepared graphene flakes, isolated single graphene sheets can be observed in the AFM images.

We have examined the thermal stability of the prepared CCG sheets and compared it with that of GO under nitrogen atmosphere using thermal gravimetric analysis (TGA). As shown in FIG. 21, the GO exhibits about 10% weight loss below 100° C. and more than 40% loss at 200° C. resulting from the removal of the labile oxygen-containing functional groups such as CO, $CO_2$ and $H_2O$ vapors.[19,20] In contrast, the CCG sheets show much higher thermal stability with no significant mass loss up to 750° C. The slight mass loss observed is probably due to the evaporation of the adsorbed water.

Figure 6A:
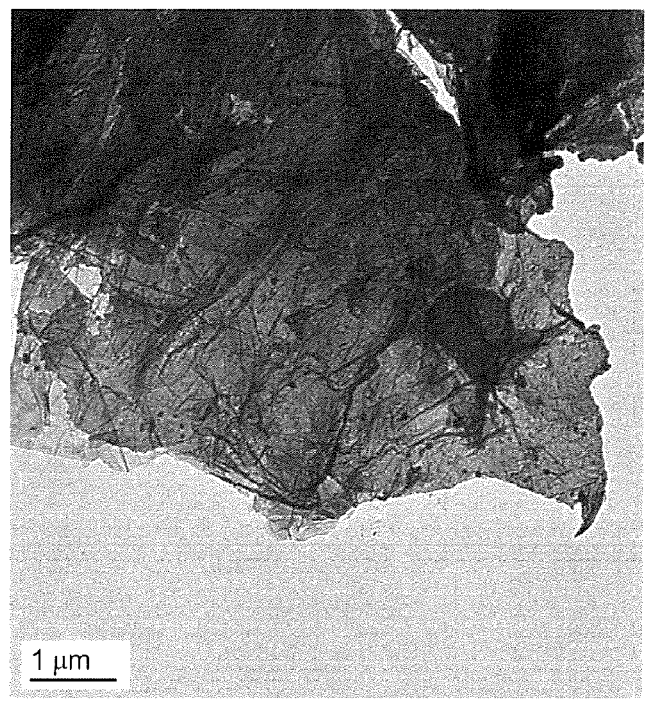
FIG. 6A-C. TEM images of graphene sheets containing 2% (wt) Pd Nanoparticles produced by MWI of solid graphite oxide containing 2% (wt) palladium nitrate. A, 1 μm scale; B, 200 nm scale; C, 100 nm scale.
Figure 6B:
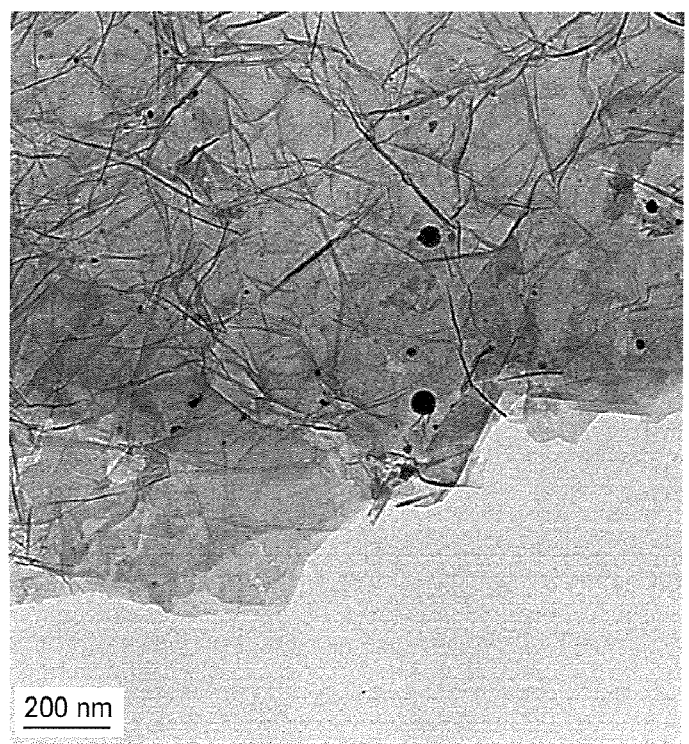
Figure 6C:
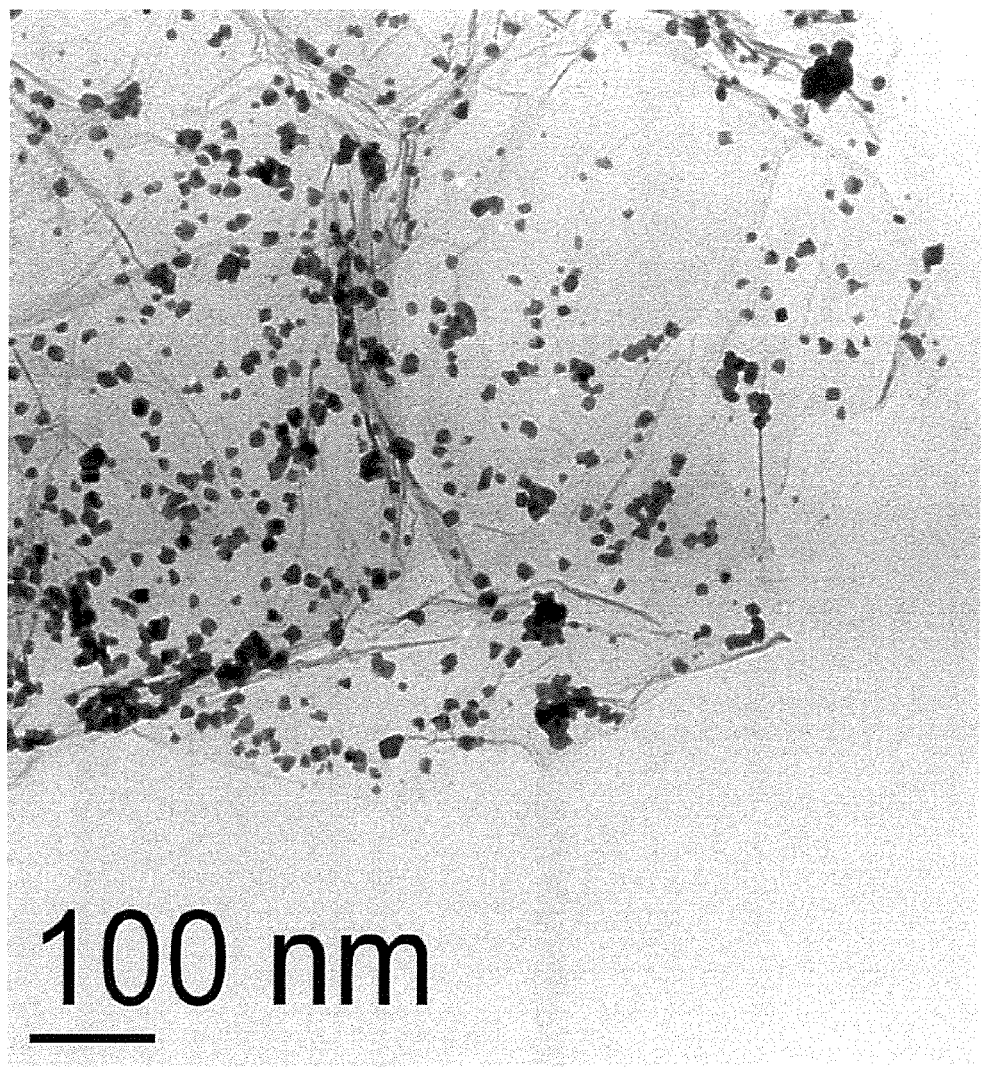

Supporting metal nanoparticles on the graphene sheets could prevent the formation of stacked graphitic structures since the metal nanoparticles can act as spacers to increase the distance between the sheets. This could lead to increasing the surface area of the nanoparticle-graphene composites.[10-12] These materials may have promising potential applications in catalysis, fuel cells, chemical sensors and hydrogen storage. To demonstrate the synthesis of these materials by the MWI method, we used two approaches to support metallic and bimetallic nanoparticles on the surface of the CCG sheets. In the first approach, hydrazine hydrate was used for the simultaneous reduction of GO and the appropriate metal salt in water. FIG. 6 displays representative TEM images of Pd, Cu and PdCu nanoparticles well-dispersed on the surface of the CCG sheets. The formation of PdCu alloy nanoparticles was confirmed by comparing the XRD pattern of the PdCu nanoparticles with that of a physical mixture of Pd and Cu nanoparticles (ESI†). The diffraction peaks of the PdCu nanoalloy are located in between the corresponding peaks of the individual metals. This suggests the formation of a solid solution corresponding to the specific nanoalloy.[37] The diffraction pattern of the nanoalloy is not simply a sum of the patterns of the individual components. It should be noted that the formation of PdCu alloy nanoparticles is thermodynamically favorable since these metals have the same fcc crystal structure with similar lattice constants. The alloy nanoparticles are likely to be formed by atom substitution of one metal for the other through diffusion processes in the solution of the reduced binary metal salts or at the interfaces of the resulting Pd and Cu nanocrystals.

The TEM images shown in FIG. 22 demonstrate the ability of our method to synthesize uniform well-dispersed metallic and bimetallic nanoparticles on the CCG sheets. The catalytic activities of these supported nanocatalysts towards CO oxidation and other catalytic reactions are currently under investigation in our laboratory.

Control experiments were performed to investigate whether the dispersion of the metal nanocrystals into the graphene sheets is due to the simultaneous reduction of the metal salts and GO during the MWI irradiation process or simply due to physical mixing of the separately prepared metal nanoparticles and graphene sheets. FIG. 23 compares TEM images of the Pd/graphene sample (images a, b, c in FIG. 23) prepared by mixing separately prepared Pd nanoparticles (using 100 ml HH and 100 ml Pd nitrate under MWI for 10-15 s) and CCG sheets (using 100 ml HH, 50 mg GO and 25 ml water under MWI for 20-25 s) with the sample (images d, e, f in FIG. 23) prepared by the simultaneous reduction of GO (50 mg in 25 ml water) and 100 ml Pd nitrate using 100 mlHH (under MWI for 20-25 s). It is clear that the simple physical mixing of the nanoparticles and graphene sheets results in significant aggregation of the metal nanoparticles with very poor dispersion on the graphene sheets. On the other hand, the simultaneous reduction of the metal salt with GO results in well dispersed nanoparticles on the graphene sheets, suggesting that specific interaction between the metal nanocrystals and the graphene sheets may be responsible for dispersion of the nanoparticles.

In the second approach, we used oleylamine or a mixture of oleylamine and oleic acid as a solvent and reducing agent for both the GO and the metal salt under MWI. In addition to being a reducing agent, oleyl amine also provides stabilization and surface passivation for the metal nanoparticles supported on the CCG sheets. The reduction of the metal ions is clearly evident by the observation of the surface plasmon resonance absorption bands as shown in FIG. 24A for the prepared Ag, Au and Cu nanoparticles supported on the CCG sheets. FIG. 24B shows representative TEM images of Au nanoparticles dispersed on the CCG sheets prepared using oleylamine as a reducing agent in the MWI method. It is clear that the highly uniform nanoparticles with a narrow size distribution are well-dispersed on the CCG sheets. By varying the ratio of the oleylamine to oleic acid during MWI of the GO in the presence of the metal ions, it is possible to control the shape of the resulting nanostructures including the formation of metal nanorods and nanowires.

It is interesting to note that the nanoparticles tend to assemble at the edges of the graphene sheets and also between the folded sheets as shown in FIG. 24B. The high surface energies of the graphene edges and steps are expected to provide highly catalytic sites for the chemisorption of gases on the metal nanoparticles. This phenomenon has been recently explored with Ag nanoparticles located at the graphene edge layers to catalyze the oxidation of neighboring carbon atoms resulting in burning a trench into the graphene layer.[38] We believe that the current approach of depositing metallic and bimetallic nanoparticles with controlled size and shape on the CCG sheets could lead to the development of efficient nanocatalysis centers localized on edges of and within the folded graphene layers.

In summary, we have developed a facile and scalable chemical reduction method assisted by microwave irradiation for the synthesis of CCG sheets and metal nanoparticles dispersed on the graphene sheets. Using this method, many types of metallic and bimetallic nanoparticles can be dispersed on the graphene sheets to create novel nanocatalysts supported on the large surface area of the thermally stable 2D graphene.

REFERENCES FOR EXAMPLE 3

1. K. S, Novoselov, A. K. Geim, S. V. Morozov, D. Jiang, Y. Zhang, S. V. Dubonos, I. V. Grigorieva and A. A. Firsov, Science, 2004, 306, 666.
2. K. S, Novoselov, A. K. Geim, S. V. Morozov, D. Jiang, M. L. Katsnelson, I. V. Grigorieva, S. V. Dubonos and A. A. Firsov, Nature, 2005, 438, 197.
3. S. Stankovich, D. A. Dikin, G. H. B. Dommett, K. M. Kohlhaas, E. J. Zimney, E. A. Stach, R. D. Piner, S. T. Nguyen and R. S. Ruoff, Nature, 2006, 442, 282.
4. C. Berger, Z. Song, X. Li, X. Wu, N. Brown, C. Naud, D. Mayou, T. Li, J. Hass, A. N. Marchenkov, A. H. Conrad, P. N. First and W. A. de Heer, Science, 2006, 312, 1191.
5. J. Wu, W. Pisula and K. Mullen, Chem. Rev., 2007, 107, 718.
6. K. S, Novoselov, Z. Jiang, Y. Zhang, S. V. Morozov, H. L. Stormer, U. Zeitler, J. C. Maan, G. S. Boebinger, P. Kim and A. K. Geim, Science, 2007, 315, 1379.
7. K. I. Bolotin, K. J. Sikes, Z. Jiamg, M. Klima, G. Fudenberg, J. Hone, P. Kim and H. L. Stormer, Solid State Commun., 2008, 146, 351.
8. T. J. Booth, P. Blake, R. R. Nair, D. Jiang, E. W. Hill, U. Bangert, A. Bleloch, M. Gass, K. S, Novoselov, M. I. Katsnelson and A. K. Geim, Nano Lett, 2008, 8, 2442.
9. C. Gomez-Navarro, M. Burghard and K. Kern, Nano Lett., 2008, 8, 2045.
10. R. Muszynski, B. Seger and P. V. Kamat, J. Phys. Chem. C., 2008, 112, 5263.
11. Y. Si and E. T. Samulski, Chem. Mater., 2008, 20, 6792.
12. G. Williams, B. Seger and P. V. Kamat, ACS Nano, 2008, 2, 1487.
13. C. Berger, Z. Song, T. Li, X. Li, A. Y. Ogbazghi, R. Feng, Z. Dai, A. N. Marchenkov, A. H. Conrad, P. N. First and W. A. de Heer, J. Phys. Chem., 2004, 108, 19912.
14. J. S. Bunch, Y. Yaish, M. Brink, K. Bolotin and P. L. McEuen, Nano Lett., 2005, 5, 287.
15. A. Malesevic, R. Vitchev, K. Schouteden, A. Volodin, L. Zhang, G. Van Tendeloo, A. Vanhulsel and C. Van Haesendonck, Nanotech., 2008, 19, 305604.
16. X. Liang, A. S. P. Chang, Y. Zhang, B. D. Harteneck, H. Choo, D. L. Olynick and S. Cabrini, Nano Left, 2008, DOI: 10.1021/n1803512z.
17. H. C. Schniepp, J. L. Li, M. J. McAllister, H. Sai, M. Herrara-Alonso, D. H. Adamson, R. K. Prud'homme, R. Car, D. A. Saville and I. A. Aksay, J. Phys. Chem. B., 2006, 110, 8535.
18. M. J. McAllister, J. L. Li, D. H. Adamson, H. C. Schniepp, A. A. Abdala, J. Liu, M. Herrara-Alonso, D. L. Milius, R. Car, R. K. Prud'homme and I. A. Aksay, Chem. Mater., 2007, 19, 4396.
19. S. Stankovich, R. D. Piner, X. Chen, N. Wu, S. T. Nguyen and R. S. Ruoff, J. Mater. Chem., 2006, 16, 155.
20. S. Stankovich, D. A. Dikin, R. D. Piner, K. M. Kohlhaas, A. Kleinhammes, Y. Jia, Y. Wu, S. T. Nguyen and R. S. Ruoff, Carbon, 2007, 45, 1558.
21. S. Gilije, S. Han, M. Wang, K. L. Wang and R. B. Kaner, Nano Left, 2007, 7, 3394.
22. B. X. Fan, W. Peng, Y. Li, X. Li, S. Wang, G. Zhang and F. Zhang, Adv. Mater., 2008, 20, 1.
23. A. Dato, V. Radmilovic, Z. Lee, J. Phillips and M. Frenklach, Nano Lett., 2008, 8, 2012.
24. J. A. Gerbec, D. Magana, A. Washington and G. F. Strouse, J. Am. Chem. Soc., 2005, 127, 15791.
25. A. B. Panda, G. P. Glaspell and M. S. El-Shall, J. Am. Chem. Soc., 2006, 128, 2790.
26. A. B. Panda, G. P. Glaspell and M. S. El-Shall, J. Phys. Chem. C., 2007, 111, 1861.
27. V. Abdelsayed; A. B. panda; G. P. Glaspell; M. S. El-Shall in Nanoparticles: Synthesis, Stabilization, Passivation, and Functionalization, ACS Symposium Series 996,2008, Eds: R. Nagarajan and T. Alan Hatton, Chapter 17, pp 225-247.
28. F. Della Negra, M. Meneghetti and E. Menna, Fullerenes, Nanotubes, and Carbon Nanostructures, 2003, 11, 25.
29. E. H. L. Falcao, R. G. Blair, J. J. Mack, L. M. Viculis, C. Kwon, M. Bendikov, R. B. Kaner, B. S. Dunn and F. Wudl, Carbon, 2007, 45, 1364.
30. W. S. Hummers Jr. and R. E. Offeman, J. Am. Chem. Soc., 1958, 80, 1339.
31. A. C. Ferrari, Solid State Commun., 2007, 446, 60.
32. S. Berciaud, S. Ryu, L. E. Brus and T. F. Heinz, Nano Lett., 2008, DOI: 0.1021/n18031444.
33. K. N. Kudin, B. Ozbas, H. C. Schniepp, R. K. Prud'home, I. A. Aksay and R. Car, Nano Lett., 2008, 8, 36.
34. M. S. Dresselhaus, G. Dresselhaus, R. Satio and A. Jorio, Phys. Rep., 2005, 409, 47.
35. D. Graf, F. Molitor, K. Ensslin, C. Stampfer, A. Jungen, C. Hierold and L. Wirtz, Nano Lett., 2007, 7, 238.
36. J. J. Wang, M. Y. Zhu, R. A. Outlaw, X. Zhao, D. M. Manos and B. C. Holloway, Appl. Phys. Lett., 2004, 85, 1265.
37. V. Abdelsayed, A. Aljarash, M. S. El-Shall, Z. A. Al Othman and A. H. Alghamdi, Chem. Mater., 2009, in press.
38. N. Severin, S. Kirstein, I. M. Sokolov and J. P. Rabe, Nano Lett., 2008, DOI: 10.1021/n18034509.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of catalyzing chemical cross-coupling of at least two reactants of interest, comprising the steps of
producing a Pd catalyst comprising nanoparticulate Pd supported on graphene by irradiating a mixture of graphite oxide (GO) and Pd metal with microwave radiation, and
combining said at least two reactants of interest in the presence of said Pd catalyst and under conditions which allow said Pd catalyst to catalyze said chemical cross-coupling of said at least two reactants of interest, wherein said chemical cross-coupling is a Heck cross-coupling reaction.

2. The method of claim 1, wherein said Pd catalyst is active for at least 5 coupling cycles.

3. The method of claim 1 wherein a product yield of said Heck cross-coupling reaction is at least 84%.

4. A method of catalyzing chemical cross-coupling of at least two reactants of interest, comprising the steps of
producing a Pd catalyst comprising nanoparticulate Pd supported on graphene by irradiating a mixture of graphite oxide (GO) and Pd metal with microwave radiation, and
combining said at least two reactants of interest in the presence of said Pd catalyst and under conditions which allow said Pd catalyst to catalyze said chemical cross-coupling of said at least two reactants of interest, wherein said chemical cross-coupling is a Sonogashira coupling reaction.

5. The method of claim 4, wherein a product yield of said Sonogashira cross-coupling reaction is at least 88%.

6. The method of claim 1, wherein said Pd catalyst is substantially free of residual contaminants.

7. A method of catalyzing chemical cross-coupling of at least two reactants of interest, comprising the steps of
producing a Pd catalyst comprising nanoparticulate Pd supported on graphene by irradiating a mixture of graphite oxide (GO) and Pd metal with microwave radiation, and
combining said at least two reactants of interest in the presence of said Pd catalyst and under conditions which allow said Pd catalyst to catalyze said chemical cross-coupling of said at least two reactants of interest, wherein said chemical cross-coupling is selected from the group consisting of a Negish reaction, a Stille reaction, and a Buchwalk-Hartwig reaction.

8. The method of claim 4, wherein said Pd catalyst is substantially free of residual contaminants.

9. The method of claim 7, wherein said Pd catalyst is substantially free of residual contaminants.

* * * * *